United States Patent [19]

Branca et al.

[11] Patent Number: 4,808,605
[45] Date of Patent: Feb. 28, 1989

[54] TETRAHYDRONAPHTHALENE DERIVATIVES AS CALCIUM ANTAGONISTS

[75] Inventors: Quirico Branca; Roland Jaunin; Hans P. Märki, all of Basel; Fränzi Marti, Riehen; Henri Ramuz, Birsfelden, all of Switzerland

[73] Assignee: Hoffmann-La Roche Inc., Nutley, N.J.

[21] Appl. No.: 119,114

[22] Filed: Nov. 10, 1987

[30] Foreign Application Priority Data

Nov. 14, 1986 [CH] Switzerland .................... 4565/86

[51] Int. Cl.$^4$ .................... A61K 31/415; C07D 413/06
[52] U.S. Cl. .................... 514/394; 514/220; 514/221; 514/234.5; 514/303; 514/338; 514/367; 514/373; 514/387; 514/395; 514/400; 540/496; 540/506; 540/507; 544/139; 546/118; 546/271; 548/161; 548/179; 548/180; 548/305; 548/329; 548/330; 548/342
[58] Field of Search .................... 514/220, 221, 300, 367, 514/373, 394, 234.5, 303, 338, 387, 395, 400; 540/496, 506, 507; 546/118, 271; 548/160, 329, 330, 161, 179, 180, 305, 342; 544/139

[56] References Cited

U.S. PATENT DOCUMENTS 3,914,216 10/1975 Bauer et al. .................... 540/506
4,680,310 7/1987 Hengartner et al. .................... 514/539

OTHER PUBLICATIONS

Chem. Abstracts 90(15):121465x (1979) (Furnefeld, E., et al., *J. Org. Chem.* 1979, 44(5), 835–839).

*Primary Examiner*—Richard A. Schwartz
*Attorney, Agent, or Firm*—Jon S. Saxe; Bernard S. Leon; Matthew Boxer

[57] ABSTRACT

Compounds of the formula

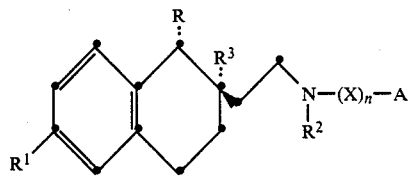

wherein R is lower-alkyl, $R^1$ is halogen, $R^2$ is $C_1$–$C_{12}$-alkyl, $R^3$ is hydroxy, lower-alkoxy, lower-alkyl-carbonyloxy, lower-alkoxy-lower-alkylcarbonoyloxy, lower-alkylaminocarbonyloxy, arylaminocarbonyloxy or aryl-lower alkylaminocarbonyloxy, X is $C_1$–$C_{18}$-alkylene which optionally can be interrupted by 1,4-phenylene or interrupted or lengthened by 1,4-cyclohexylene, A is di- or tri-substituted 2-imidazolyl attached via an ethylene group or a substituted or unsubstituted heterocycle selected from the group consisting of benzimidazolyl, benzimidazolonyl, imidazo[4,5-c]pyridinyl, imidazo[4,5-c]pyridinonyl, benzthiazolyl, benzodiazepine-2,5-dion-1-yl and pyrrolo[2,1-c]-[1,4]benzodiazepine-5,11-dion-10-yl and n is the number 0 or 1, in the form of racemates and optical antipodes, as well as N-oxides and pharmaceutically usable acid addition salts thereof. The compounds of formual I have a pronounced calcium-antagonistic and anti-arrhythmic activity and can accordingly be used as medicaments, especially for the control or prevention of angina pectoris, ischaemia, arrhythmias, high blood pressure and cardiac insufficiency.

21 Claims, No Drawings

TETRAHYDRONAPHTHALENE DERIVATIVES AS CALCIUM ANTAGONISTS

BRIEF SUMMARY OF THE INVENTION

The invention relates to tetrahydronaphthalene derivatives of the formula

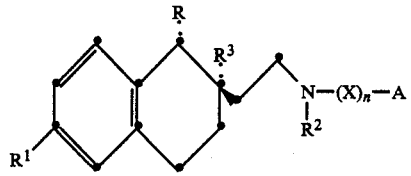

I wherein R is lower-alkyl, $R^1$ is halogen, $R^2$ is $C_1-C_{12}$-alkyl, $R^3$ is hydroxy, lower-alkoxy, lower-alkylcarbonyloxy, lower-alkoxy-lower-alkylcarbonyloxy, lower-alkylaminocarbonyloxy, arylaminocarbonyloxy or aryl-lower-alkylaminocarbonyloxy, X is $C_1-C_{18}$-alkylene, $C_1-C_{18}$-alkylene which is interrupted by 1,4-phenylene or interrupted or lengthened by 1,4-cyclohexylene, A is di- or tri-substituted 2-imidazolyl attached via an ethylene group or a substituted or unsubstituted heterocycle selected from the group consisting of benzimidazolyl, benzimidazolonyl, imidazo[4,5-c]pyridinyl, imidazo[4,5-c]-pyridinonyl, benzthiazolyl, benzodiazepine-2,5-dion-1-yl and pyrrolo[2,1-c][1,4]benzodiazepine-5,11-dion-10-yl and n is the number 0 or 1, in the form of racemates and optical antipodes, as well as N-oxides and pharmaceutically usable acid addition salts thereof.

The compounds of formula I are useful as agents for the treatment or prevention of angina pectoris, ischaemia, arrhythmias, high blood pressure and cardiac insufficiency.

DETAILED DESCRIPTION OF THE INVENTION

As used herein, the term "lower-alkyl"—alone or in combination—denotes straight-chain and branched, saturated hydrocarbon groups with 1-6, preferably 1-4, carbon atoms such as methyl, ethyl, n-propyl, isopropyl, n-butyl, isobutyl, sec.-butyl, tert.-butyl and the like. The term "$C_1-C_{12}$-alkyl" denotes straight-chain and branched, saturated hydrocarbon groups with 1-12 carbon atoms. The term "lower-alkoxy" denotes lower-alkyl ether groups in which the term "lower-alkyl" is as described above. The term "halogen" denotes the four halogen atoms fluorine, chlorine, bromine and iodine. The term "$C_1-C_{18}$-alkylene" denotes straight-chain or branched saturated hydrocarbon groups with 1-18 carbon atoms such as methylene, ethylene, propylene, methylethylene, butylene, 1,1-dimethylpropylene, pentamethylene, 1-methylpentamethylene, hexamethylene, heptamethylene, undecamethylene and the like. The term "aryl" denotes phenyl optionally mono- or multiply-substituted by halogen, trifluoromethyl, lower-alkyl, lower-alkoxy, nitro or amino. The term "aryl-lower-alkyl" denotes straight-chain or branched lower-alkyl groups in which one or more hydrogen atoms is/are replaced by aryl groups, such as benzyl, phenethyl and the like. Examples of optionally substituted benzimidazolyl, benzimidazolonyl, imidazo[4,5-c]pyridinyl, imidazo[4,5-c]pyridinonyl, benzthiazolyl, benzodiazepine-2,5-dion-1-yl or pyrrolo[2,1-c][1,4]benzodiazepine-5,11-dion-10-yl are 2-benzimidazolyl, 1-methyl-2-benzimidazolyl, 1-dodecyl-2-benzimidazolyl, benzimidazolonyl, 3-methylbenzimidazolonyl, 3-isopropylbenzimidazolonyl, 3-butylbenzimidazolonyl, 3-morpholinoethylbenzimidazolonyl, 3-benzylbenzimidazolonyl, 2-pyridylmethylbenzimidazolonyl, 2-imidazo[4,5-c]pyridinyl, imidazo[4,5-c]pyridinonyl, 2-benzthiazolyl, 2,3,4,5-tetrahydro-4-methylbenzodiazepine-2,5-dion-1-yl, 6-chloro-2,3,11,11a-tetrahydropyrrolo[2,1-c][1,4]benzodiazepine-5,11-dion-10-yl, 5,6-dimethyl-2-benzimidazolyl and the 106 like. Examples of di- and tri-substituted 2-imidazolyl attached via an ethylene group are 1-methyl-4,5-diphenyl-2-imidazolylethyl and 4,5-diphenyl-2-imidazolylethyl and the like. The term "leaving group" denotes conventional leaving groups such as halogen, preferably chlorine or bromine, arylsulphonyloxy such as, for example, tosyloxy, bromobenzenesulphonyloxy, benzenesulphonyloxy or mesitylenesulphonyloxy, or alkylsulphonyloxy such as, for example, mesyloxy or trifluoromethylsulphonyloxy. The term "N-oxide" denotes a compound wherein the nitrogen which is oxidized is the nitrogen which is attached via an ethylene to the tetrahydronaphthalene moiety. The terminology that X is $C_1-C_{18}$ alkylene which can be interrupted by 1,4-phenylene denotes that the moiety, X, can be

wherein the total number of carbon atoms in the two alkylene moieties together is not greater than 18. The terminology that X is $C_1-C_{18}$ alkylene which can be interrupted or lengthened by 1,4-cyclohexylene denotes that the moiety, X, can be

or that X can be an alkylene moiety with cyclohexylene attached either to the A moiety or the

moiety.

The term "pharmaceutically usable acid addition salt" denotes salts with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like. Such salts can be manufactured readily by any person skilled in the art having regard to the state of the art and taking into consideration the nature of the compound to be converted into a salt.

The invention relates to tetrahydronaphthalene derivatives of the formula

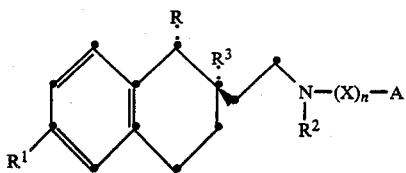

wherein R is lower-alkyl, $R^1$ is halogen, $R^2$ is $C_1$-$C_{12}$-alkyl, $R^3$ hydroxy, lower-alkoxy, lower-alkylcarbonyloxy, lower-alkoxy-lower-alkylcarbonyloxy, lower-alkylaminocarbonyloxy, arylaminocarbonyloxy or aryl-lower-alkylaminocarbonyloxy, X is $C_1$-$C_{18}$-alkylene, $C_1$-$C_{18}$-alkylene which is interrupted by 1,4-phenylene or interrupted or lengthened by 1,4-cyclohexylene, A is di- or tri-substituted 2-imidazolyl attached via an ethylene group or benzimidazolyl, substituted benzimidazolyl, benzimidazolonyl, imidazo[4,5-c]pyridinyl, imidazo[4,5-c]pyridinonyl, benzthiazolyl, benzodiazepine-2,5-dion-1-yl or pyrrolo[2,1-c][1,4]benzodiazepine-5,11-dion-10-yl and n is the number 0 or 1, in the form of racemates and optical antipodes, as well as N-oxides and pharmaceutically usable acid addition salts thereof.

The compounds of formula I are useful as calcium antagonists. More specifically, the compounds of formula I are useful as agents in the treatment or prevention of angina pectoris, ischaemia, arrhythmias, high blood pressure and cardiac insufficiency.

Those compounds of formula I in which R is isopropyl are preferred. $R^3$ preferably is hydroxy, lower-alkylcarbonyloxy, particularly isobutyryloxy, lower-alkoxy-lower-alkylcarbonyloxy, particularly methoxyacetyloxy, or lower-alkylaminocarbonyloxy, particularly butylaminocarbonyloxy. n preferably is the number 1. Further, those compounds of formula I in which $R^1$ is fluorine are preferred. Those compounds of formula I in which $R^2$ is methyl are also preferred. The compounds of formula I in which X is $C_3$-$C_7$-alkylene, particularly propylene, butylene, pentamethylene or hexamethylene, are likewise preferred. A preferably signifies 2-benzimidazolyl, 2-benzthiazolyl, 1-methyl-2-benzimidazolyl, 1-dodecyl-2-benzimidazolyl, benzimidazolonyl, 2,3,4,5-tetrahydro-4-methylbenzodiazepine-2,5-dion-1-yl, 6-chloro-2,3,11,11a-tetrahydro-pyrrolo[2,1-c][1,4]benzodiazepine-5,11-dion-10-yl or 1-methyl-4,5-diphenyl-2-imidazolyl, particularly 2-benzimidazolyl or 2-benzthiazolyl.

More, preferred are those compounds of formula I in which R is isopropyl, $R^3$ is hydroxy, isobutyryloxy, methoxyacetyloxy or butylaminocarbonyloxy, $R^1$ is fluorine, $R^2$ is methyl, X is propylene, butylene, pentamethylene or hexamethylene, A is 2-benzimidazolyl or 2-benzthiazolyl and n is the number 1.

Especially preferred compounds of formula I are:
2-[2-[[3-(2-Benzimidazolyl)propyl]methylamino]ethyl]-6-fluoro-1,2,3,4-tetrahydro-1α-isopropyl-2α-naphthyl methoxyacetate;
[1S,2S]-2-[2-[[5-(2-benzthiazolyl)pentyl]methylamino]ethyl]-6-fluoro-1,2,3,4-tetrahydro-1-isopropyl-2-naphthyl methoxyacetate; and
[1S,2S]-2-[2-[[3-(2-benzimidazolyl)propyl]methylamino]ethyl]-6-fluoro-1,2,3,4-tetrahydro-1-isopropyl-2-naphthyl methoxyacetate.

Exemplary of other compounds of formula 1 are:

[1S,2S]-2-[2-[[7-(2-benzimidazolyl)heptyl]methylamino]-ethyl]-6-fluoro-1,2,3,4-tetrahydro-1-isopropyl-1-naphthalenol;
[1S,2S]-6-fluoro-1,2,3,4-tetrahydro-1-isopropyl-2-[2-[methyl-[5-(1-methyl-2-benzimidazolyl)pentyl]amino]ethyl]-2-naphthyl butylcarbamate;
[1S,2S]-6-fluoro-1,2,3,4-tetrahydro-1-isopropyl-2-[2-[methyl-[6-(2-oxo-1-benzimidazolinyl)hexyl]amino]ethyl]-2-naphthyl methoxyacetate;
[1S,2S]-2-[2-[[3-(2-benzimidazolyl)propyl]methyl-N-oxidoamino]ethyl]-6-fluoro-1,2,3,4-tetrahydro-1-isopropyl-2-naphthyl methoxyacetate;
[1S,2S]-2-[2-[[7-(1-dodecyl-2-benzimidazolyl)heptyl]methylamino]ethyl]-6-fluoro-1,2,3,4-tetrahydro-1-isopropyl-2-naphthyl methoxyacetate;
[1S,2S]-6-fluoro-1,2,3,4-tetrahydro-1-isopropyl-2-[2-[[3-(1-methyl-4,5-diphenylimidazol-2-yl)propyl]methylamino]ethyl]-2-naphthyl methoxyacetate:
[1S,2S]-6-fluoro-1,2,3,4-tetrahydro-1-isopropyl-2-[2-[[4-[(2-benzimidazolyl)methyl]benzyl]methylamino]ethyl]-2-naphthyl methoxyacetate;
[1S,2S]-2-[2-[[3-(2-benzimidazolyl)propyl]methylamino]ethyl]-6-fluoro-1,2,3,4-tetrahydro-1-isopropyl-2-naphthalenol;
[1S,2S]-2-[2-[[3-(2-benzimidazolyl)propyl]methylamino]ethyl]-6-fluoro-1,2,3,4-tetrahydro-1-isopropyl-2-naphthyl methoxyacetate;
[1S,2S]-2-[2-[[5-(2-benzimidazoly)pentyl]methylamino]ethyl]-6-fluoro-1,2,3,4-tetrahydro-1-isopropyl-2-naphthalenol;
[1S,2S]-2-[2-[[5-(2-benzimidazolyl)pentyl]methylamino]ethyl]-6-fluoro-1,2,3,4-tetrahydro-1-isopropyl-2-naphthyl methoxyacetate; [1S,2S]-2-[2-[[4-(2-benzimidazoly)butyl]methylamino]ethyl]-6-fluoro-1,2,3,4-tetrahydro-1-isopropyl-2-naphthalenol;
[1S,2S]-2-[2-[[11-(2-benzimidazolyl)undecyl]methylamino]ethyl]-6-fluoro-1,2,3,4-tetrahydro-1-isopropyl-2-naphthalenol;
[1S,2S]-2-[2-[[7-(5,6-dimethyl-2-benzimidazolyl)heptyl]methylamino]ethyl]-6-fluoro-1,2,3,4-tetrahydro-1-isopropyl-2-naphthalenol;
[1S,2S]-2-[2-[[5-(2-benzimidazolyl)pentyl]dodecylamino]ethyl]-6-fluoro-1,2,3,4-tetrahydro-1-isopropyl-2-naphthalenol;
[1S,2S]-6-fluoro-1,2,3,4-tetrahydro-1-isopropyl-2-[2-[[7-(1H-imidazo[4,5-c]pyridin-2-yl)heptyl]methylamino]ethyl]-2-naphthalenol;
[1S,2S]-2-[2-[[4-(2-Benzimidazolyl)butyl]methylamino]ethyl]-6-fluoro-1,2,3,4-tetrahydro-1-isopropyl-2-naphthyl methoxyacetate;
[1S,2S]-2-[2-[[7-(2-benzimidazolyl)heptyl]methylamino]ethyl]-6-fluoro-1,2,3,4-tetrahydro-1-isopropyl-2-naphthyl methoxyacetate;
[1S,2S]-2-[2-[[11-(2-benzimidazolyl)undecyl]methylamino]ethyl]-6-fluoro-1,2,3,4-tetrahydro-1-isopropyl-2-naphthyl methoxyacetate;
[1S,2S]-2-[2-[[7-(5,6-dimethyl-2-benzimidazolyl)heptyl]methylamino]ethyl]-6-fluoro-1,2,3,4-tetrahydro-1-isopropyl-2-naphthyl methoxyacetate;
[1S,2S]-2-[2-[[5-(2-benzimidazolyl)pentyl]dodecylamino]ethyl]-6-fluoro-1,2,3,4-tetrahydro-1-isopropyl-2-naphthyl methoxyacetate;
[1S,2S]-6-fluoro-1,2,3,4-tetrahydro-1-isopropyl-2-[2-[[7-(1H-imidazo[4,5-c]pyridin-2-yl)heptyl]methylamino]ethyl]-2-naphthyl methoxyacetate;
[1S,2S]-2-[2-[[3-(2-benzthiazolyl)propyl]methylamino]ethyl]-6-fluoro-1,2,3,4-tetrahydro-1-isopropyl-2-naphthalenol;

[1S,2S]-2-[2-[[5-(2-benzthiazolyl)pentyl]methylamino]ethyl]-6-fluoro-1,2,3,4-tetrahydro-1-isopropyl-2-naphthalenol;

[1S,2S]-2-[2-[[7-(2-benzthiazolyl)heptyl]methylamino]ethyl]-6-fluoro-1,2,3,4-tetrahydro-1-isopropyl-2-naphthalenol;

[1S,2S]-2-[2-[[3-(2-benzthiazolyl)propyl]methylamino]ethyl]-6-1,2,3,4-tetrahydro-1-isopropyl-2-naphthyl methoxyacetate;

[1S,2S]-2-[2-[[7-(2-benzthiazolyl)heptyl]methylamino]ethyl-6-fluoro-1,2,3,4-tetrahydro-1-isopropyl-2-naphthyl methoxyacetate;

[1S,2S]-2-[2-[[(S)-5-(2-benzimidazolyl)-1-methylpentyl]methylamino]ethyl-6-fluoro-1,2,3,4-tetrahydro-1-isopropyl-2-naphthalenol;

[1S,2S]-2-[2-[[(S)-5-(2-benzimidazolyl)-1-methylpentyl]methylamino]ethyl-6-fluoro-1,2,3,4-tetrahydro-1-isopropyl-2-naphthyl methoxyacetate;

[1S,2S]-2-[2-[[7-(2-benzimidazolyl)heptyl]methylamino]ethyl]-6-fluoro-1,2,3,4-tetrahydro-1-isopropyl-2-methoxynaphthalenol;

[1S,2S]-6-fluoro-1,2,3,4-tetrahydro-1-isopropyl-2-[2-[methyl-5-(1-methyl-2-benzimidazolyl)pentyl]amino]ethyl]-2-naphthalenol;

[1S,2S]-2-[2-[[7-(1-dodecyl-2-benzimidazolyl)heptyl]methylamino]ethyl]-6-fluoro-1,2,3,4-tetrahydro-1-isopropyl-2-naphthalenol;

[1S,2S]-6-fluoro-1,2,3,4-tetrahydro-1-isopropyl-2-[2-methyl-5-(1-methyl-2-benzimidazolyl)pentyl]amino]ethyl]-2-naphthyl methoxyacetate;

[1S,2S]-2-[2-[(2-benzthiazolyl)methylamino]ethyl]-6-fluoro-1,2,3,4-tetrahydro-1-isopropyl-2-naphthalenol;

1-[2-[[2-[[1S,2S]-6-fluoro-1,2,3,4-tetrahydro-2-hydroxy-1-isopropyl-2-naphthyl]ethyl]methylamino]ethyl]-2-benzimidazolinone;

[1S,2S]-6-fluoro-1,2,3,4-tetrahydro-1-isopropyl-2-[2-[methyl-[2-(2-oxo-1-benzimidazolinyl)ethyl]amino]ethyl]-2-naphthyl methoxyacetate;

1-[6-[[2-[[1S,2S]-6-fluoro-1,2,3,4-tetrahydro-2-hydroxy-1-isopropyl-2-naphthyl]ethyl]methylamino]hexyl]-2-benzimidazolinone;

1-[6-[[2-[[1S,2S]-6-fluoro-1,2,3,4-tetrahydro-2-hydroxy-1-isopropyl-2-naphthyl]ethyl]methylamino]hexyl]-3-methyl-2-benzimidazolinone;

[1S,2S]-6-fluoro-1,2,3,4-tetrahydro-1-isopropyl-2-[2-[[4-[p-(imidazol-1-yl)phenyl]butyl]methylamino]ethyl]-2-naphthalenol;

1-[4-[[2-[[1S,2S]-6-fluoro-1,2,3,4-tetrahydro-2-hydroxy-1-isopropyl-2-naphthyl]ethyl]methylamino]butyl]-2-benzimidazoline;

1-[4-[[2-[[1S,2S]-6-fluoro-1,2,3,4-tetrahydro-2-hydroxy-1-isopropyl-2-naphthyl]ethyl]methylamino]butyl]-3-isopropropyl-2-benzimidazolinone;

1-[6-[[2-[[1S,2S]-6-fluoro-1,2,3,4-tetrahydro-2-hydroxy-1-isopropyl-2-naphthyl]ethyl]methylamino]hexyl]-3-butyl-2-benzimidazolinone;

1-[6-[[2-[[1S,2S]-6-fluoro-1,2,3,4-tetrahydro-2-hydroxy-1-isopropyl-2-naphthyl]ethyl]methylamino]hexyl]-3-(2-morpholinoethyl)-2-benzimidazolinone;

1-benzyl-3-[4-[[2-[[1S,2S]-6-fluoro-1,2,3,4-tetrahydro-2-hydroxy-1-isopropyl-2-naphthyl]ethyl]methylamino]butyl]-2-benzimidazolinone;

1-[4-[[2-[[1S,2S]-6-fluoro-1,2,3,4-tetrahydro-2-hydroxy-1-isopropyl-2-naphthyl]ethyl]methylamino]butyl]-3-(2-pyridylmethyl)-2-benzimidazolinone;

3-[6-[[2-[[1S,2S]-6-fluoro-1,2,3,4-tetrahydro-2-hydroxy-1-isopropyl-2-naphthyl]ethyl]methylamino]hexyl]-1,3-dihydro-2H-imidazo[4,5-c]pyridin-2-one;

[1S,2S]-6-fluoro-1,2,3,4-tetrahydro-1-isopropyl-2-[2-[methyl-[4-(2-oxo-1-benzimidazolinyl)butyl]amino]ethyl]-2-naphthyl methoxyacetate;

[1S,2S]-2-[2-[[6-(1,2-dihydro-2-oxo-3H-imidazo[4,5-c]pyridin-3-yl)hexyl]methylamino]ethyl]-6-fluoro-1,2,3,4-tetrahydro-1-isopropyl-2-naphthyl methoxyacetate;

[1S,2S]-6-fluoro-1,2,3,4-tetrahydro-1-isopropyl-2-[2-[methyl-[6-(3-methyl-2-oxo-1-benzimidazolinyl)hexyl]amino]ethyl]-2-naphthyl methoxyacetate;

[1S,2S]-6-fluoro-1,2,3,4-tetrahydro-1-isopropyl-2-[2-[[4-[p-(imidazol-1-yl)phenyl]butyl]methylamino]ethyl]-2-naphthyl methoxyacetate;

[1S,2S]-6-fluoro-1,2,3,4-tetrahydro-1-isopropyl-2-[2-[methyl-[4-(3-isopropyl-2-oxo-1-benzimidazolinyl)butyl]amino]ethyl]-2-naphthyl methoxyacetate;

[1S,2S]-6-fluoro-1,2,3,4-tetrahydro-1-isopropyl-2-[2-[methyl-[6-(3-butyl-2-oxo-1-benzimidazolinyl)hexyl]amino]ethyl]-2-naphthyl methoxyacetate;

[1S,2S]-6-fluoro-1,2,3,4-tetrahydro-1-isopropyl-2-[2-[methyl-[6-[3-(2-morpholinoethyl)-2-oxo-1-benzimidazolinyl]hexyl]amino]ethyl]-2-naphthyl methoxyacetate;

[1S,2S]-2-[2-[[4-(3-benzyl-2-oxo-1-benzimidazolinyl)butyl]methylamino]ethyl]-6-fluoro-1,2,3,4-tetrahydro-1-isopropyl-2-naphthyl methoxyacetate;

[1S,2S]-6-fluoro-1,2,3,4-tetrahydro-1-isopropyl-2-[2-[methyl-[4-[2-oxo-3-(2-pyridylmethyl)-1-benzimidazolinyl]butyl]amino]ethyl]-2-naphthyl methoxyacetate;

[1S,2S]-2-[2-[[3-(2-benzimidazolyl)propyl]methylamino]ethyl]-6-fluoro-1,2,3,4-tetrahydro-1-isopropyl-2-naphthyl isobutyrate;

[1S,2S]-6-fluoro-1,2,3,4-tetrahydro-1-isopropyl-2-[2-[methyl-[5-(1-methyl-2-benzimidazolyl)pentyl]amino]ethyl]-2-naphthyl carbanilate;

[1S,2S]-6-fluoro-1,2,3,4-tetrahydro-1-isopropyl-2-[2-[methyl-[5-(1-methyl-2-benzimidazolyl)pentyl]amino]ethyl]-2-naphthyl benzylcarbamate;

[1S,2S]-6-fluoro-1,2,3,4-tetrahydro-1-isopropyl-2-[2-[methyl-[5-(1-methyl-2-benzimidazolyl)pentyl]amino]ethyl]-2-naphthyl p-chlorocarbanilate;

[1S,2S]-6-fluoro-1,2,3,4-tetrahydro-1-isopropyl-2-[2-[[3-(4,5-diphenylimidazol-2-yl)propyl]methylamino]ethyl]-2-naphthyl methoxyacetate;

[1S,2S]-6-fluoro-1,2,3,4-tetrahydro-1-isopropyl-2-[2-[[4-[(1-methyl-2-benzimidazolyl)methyl]benzyl]methylamino]ethyl]-2-naphthyl methoxyacetate;

[1S,2S]-6-fluoro-1,2,3,4-tetrahydro-1-isopropyl-2-[2-[[4-[1-(1-methyl-2-benzimidazolyl)ethyl]benzyl]methylamino]ethyl]-2-naphthyl methoxyacetate;

[1S,2S]-6-fluoro-1,2,3,4-tetrahydro-1-isopropyl-2-[2-[methyl-[trans-4-(2-benzimidazolyl)cyclohexyl]methylamino]ethyl]-2-naphthyl methoxyacetate;

[1S,2S]-6-fluoro-1,2,3,4-tetrahydro-1-isopropyl-2-[2-[methyl-[trans-4-(1-methyl-2-benzimidazolyl)cyclohexyl]methylamino]ethyl]-2-naphthyl methoxyacetate;

1-[4-[[2-[[1S,2S]-6-fluoro-1,2,3,4-tetrahydro-2-hydroxy-1-isopropyl-2-naphthyl]ethyl]methylamino]butyl]-3,4-dihydro-4-methyl-2H-1,4-benzodiazepine-2,5(1H)-dione;

(S)-6-chloro-10-[4-[[2-[[1S,2S]-6-fluoro-1,2,3,4-tetrahydro-2-hydroxy-1-isopropyl-2-naphthyl]ethyl]methylamino]butyl]-1,2,3,11a-tetrahydro-5H-pyrrolo[2,1-c][1,4]benzodiazepine-5,11-(10H)-dione;

[1S,2S]-6-fluoro-1,2,3,4-tetrahydro-1-isopropyl-2-[2-[[4-(2,3,4,5-tetrahydro-4-methyl-2,5-dioxo-1H-1,4-benzodiazepin-1-yl)butyl]methylamino]ethyl]-2-naphthyl methoxyacetate; and

[1S,2S]-2-[2-[[4-[(S)-6-chloro-2,3,11,11a-tetrahydro-5,-11-dioxo-1H-pyrrolo[2,1-c][1,4]benzodiazepin-10(5H)yl]butyl]methylamino]ethyl]-6-fluoro-1,2,3,4-tetrahydro-1-isopropyl-2-naphthyl methoxyacetate.

The compounds of formula I in the form of racemates and optical antipodes, as well as N-oxides and pharmaceutically usable acid addition salts thereof can be prepared as follows:

(a) for the making of compounds of formula I in which $R^3$ is hydroxy or lower-alkoxy and R, $R^1$, $R^2$, A, X and n are as described above, reacting a compound of the formula

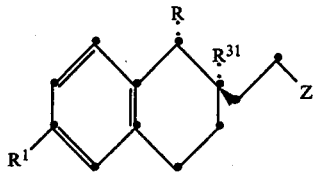

II wherein $R^{31}$ is hydroxy or lower-alkoxy and Z is a leaving group and R and $R^1$ are as described above, with an amine of the formula

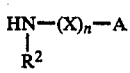

III wherein $R^2$, A, X and n are as described above, or (b) for the making of compounds of formula I in which $R^3$ is lower-alkylcarbonyloxy or lower-alkoxy-lower-alkylcarbonyloxy and R, $R^1$, $R^2$, A, X and n are as described above reacting a compound of the formula

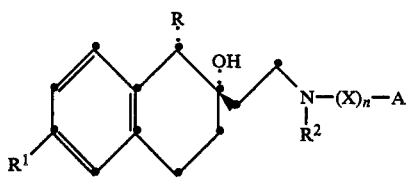

Ia wherein R, $R^1$, $R^2$, A, X and n are as described above, with an acylating agent yielding a lower-alkylcarbonyl or lower-alkoxy-lower-alkylcarbonyl group, or (c) for the making of compounds of formula I in which $R^3$ is lower-alkylaminocarbonyloxy, arylaminocarbonyloxy or aryl-lower-alkylaminocarbonyloxy and R, $R^1$, $R^2$, A, X and n are as described above, reacting a compound of formula Ia above with a lower-alkyl, aryl or aryl-lower-alkyl isocyanate, and, if desired, (d) oxidizing a compound obtained to the corresponding N-oxide, and/or (e) separating a racemate obtained into the optical antipodes, and/or (f) converting a compound obtained into a pharmaceutically usable acid addition salt.

A compound of formula II is reacted with an amine of formula III according to conventional methods. The reaction is carried out in the presence or absence of an organic solvent which is inert under the reaction conditions at a temperature between about 20° and 150° C., preferably between about 80° and 120° C. Solvents such as dimethylformamide, dimethyl sulphoxide, alcohols such as isopropanol or tert.-butanol, ethers such as tetrahydrofuran or dioxan, aromatic hydrocarbons such as benzene, toluene or xylene, chlorinated hydrocarbons such as methylene chloride, carbon tetrachloride or chlorobenzene, and the like come into consideration in this reaction. The reaction is advantageously carried out in the presence of an acid-binding agent, for example a tertiary amine such as trimethylamine, triethylamine, ethyldiisopropylamine or 1,5-diazabicyclo[4.3.0]-non-5-ene, whereby excess amine of formula III can also serve as the acid-binding agent. For reasons of convenience the reaction is carried out at atmospheric pressure, although higher pressure can also be used.

The acylation of a compound of formula Ia is also carried out according to conventional methods. Suitable acylating agents are, in particular, activated acid derivatives such as acid halides and acid anhydrides or mixed acid anhydrides. The reaction is carried out in an organic solvent or solvent mixture which is inert under the reaction conditions at a temperature between about 0° C. and the reflux temperature. As solvents there come into consideration, in particular, aromatic hydrocarbons such as benzene, toluene or xylene, chlorinated hydrocarbons such as methylene chloride or chloroform, ethers such as diethyl ether, tetrahydrofuran or dioxan, and the like.

The reaction of a compound of formula Ia with an isocyanate can also be effected according to conventional methods in an organic solvent or solvent mixture which is inert under the reaction conditions at a temperature between about 50° C. and the boiling point of the solvent or solvent mixture, preferably between about 80° and 120° C., in the presence of a catalyst such as a tin-(II) salt, e.g. tin-(II) 2-ethylhexanoate. As solvents there come into consideration, in particular, aromatic hydrocarbons such as benzene, toluene or xylene, ethers such as tetrahydrofuran or dioxan, and the like.

A compound obtained can be converted into the corresponding N-oxide likewise in a conventional manner by means of an oxidation agent such as hydrogen peroxide or a peracid such as peracetic acid or perbenzoic acidiin a solvent such as an alkanol, e.g. methanol or ethanol, and the like at a temperature between about 0° and 50° C., preferably at room temperature.

The starting materials of formulae II and III are known or can be obtained in accordance with known methods. A process for the preparation of a compound of formula III in which A is a heterocycle attached via a nitrogen atom or a carbon atom or di- or tri-substituted 2-imidazolyl attached via an ethylne group is outlined in Schemes I-III hereinafter in which Boc denotes tert.butoxycarbonyl, Bz denotes benzyl and Ph denotes phenyl. With respect to the precise reaction conditions, reference is made to the experimental section.

The starting materials of formula IV, XI and XV in Schemes I-III are known.

Scheme I $H_2N-(CH_2)_6-OH$     IV

↓

$Boc-NH-(CH_2)_6OH$     V

↓

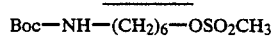
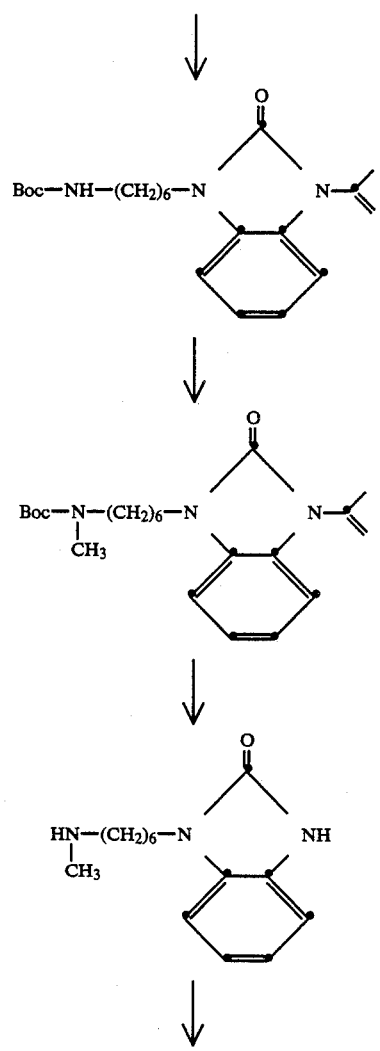
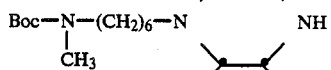
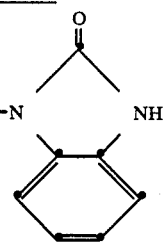
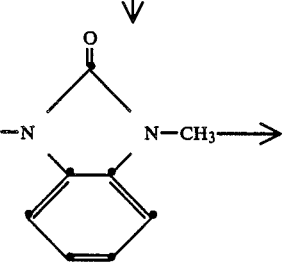
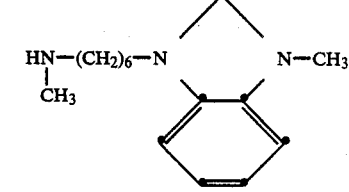
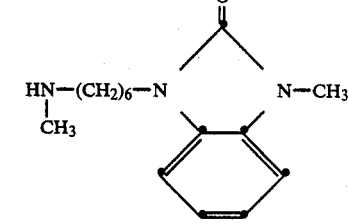
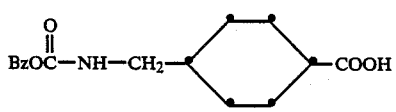
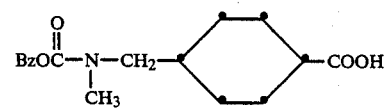

-continued
Scheme II

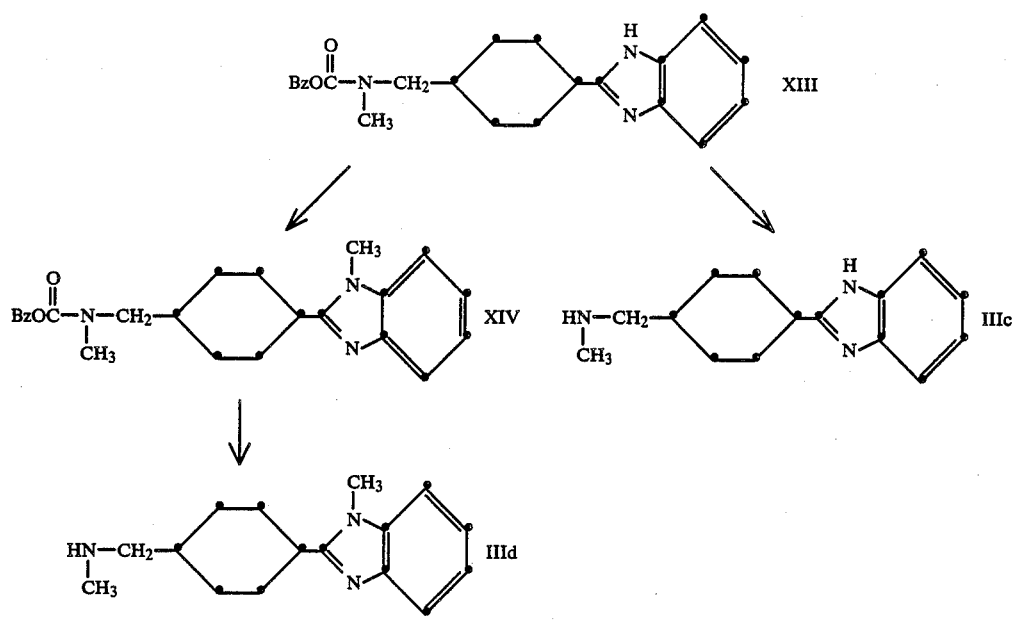

Scheme III

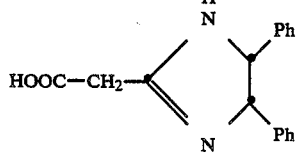 XV

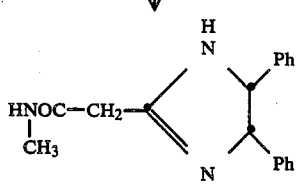 XVI

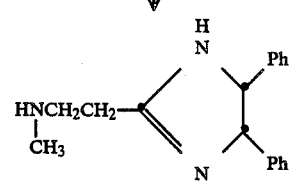 IIIe

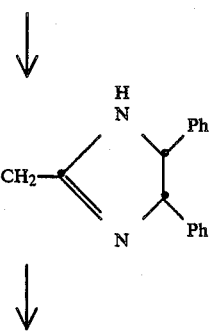 XVII

-continued
Scheme III

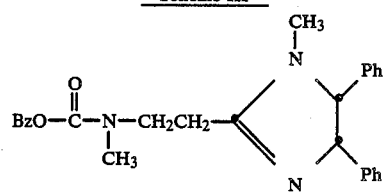 XVIII

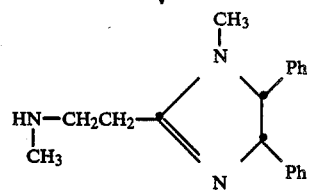 IIIf

The compounds of formula I contain at least one asymmetric centre (2-position) and can therefore exist as optical antipodes or as racemates. Compounds of formula I which contain more than one asymmetric centre are present in the relative configuration indicated by formula I. The racemates of formula I can be resolved into the optical antipodes according to conventional methods, e.g. by reaction with an optically active acid and fractional crystallization of the salt obtained.

The compounds of formula I are characterized by valuable pharmacodynamic properties. In particular, the compounds of formula I have a pronounced calcium-antagonistic activity and can accordingly be used as medicaments, especially for the control or prevention of angina pectoris, ischaemia, arrhythmias, high blood pressure and cardiac insufficiency.

The calcium-antagonistic activity as well as the blood pressure-lowering properties of the compounds in accordance with the invention can be demonstrated in the tests described hereinafter:

A. $^3$H-Desmethoxyverapamil binding determinations:

The determination is carried out on partially-cleaned membranes of guinea pig heart. The reaction mixture (0.3 ml) consists of 0.2–0.8 mg of membrane protein, 2.5 nM of $^3$H-desmethoxyverapamil and various concentrations of test substances. The incubation lasts 120 minutes at 37° C. and is stopped by dilution with the incubation buffer; a filtration is subsequently carried out. The filter-bound radioactivity is measured with a scintillation counter. Specific binding (i.e. receptor-bound) is defined as the difference between total and unspecific-bound radioactivity. The unspecific binding is determined in the presence of an excess of non-radioactive verapamil (10 μM).

The activity (potency) of a compound in this test is defined by the IC$_{50}$ value. The IC$_{50}$ is the substance concentration (in mol/l) which produces a half-maximum inhibition of the specific $^3$H-desmethoxyverapamil binding. This value is extrapolated from a concentration-binding curve.

B. Isolated, perfused guinea pig heart according to Langendorff:

Guinea pigs weighing approximately 400 g are narcotized with Urethan (1 g/kg i.p.) and the heart is removed rapidly. The aorta is cannulated and the heart is perfused retrogradely with a modified Krebs-Henseleit solution of the following composition in mM: NaCl 114.7, KCl 4.7, MgSO$_4$ 1.2, KH$_2$PO$_4$ 1.5, NaHCO$_3$ 25, CaCl$_2$ 2.5 and glucose 11.1. The solution is gassed with Oxycarbon (a mixture of 95% oxygen and 5% carbon dioxide) at pH 7.3 and a temperature of 37° C. The perfusion pressure is held constant at a value of 90 cm H$_2$O (8.83 kpa). A Miller microtip catheter pressure transducer (PC-350) is inserted in the left heart chamber in order to measure the left ventricular pressure. The total coronary artery flow is collected in a funnel and measured with an electro magnetic flow meter. All measurement parameters are recorded on a recording apparatus (Gould, Model 2800). The test begins after an adaptation of 45 minutes. Substances are infused with a velocity of 1% of the total coronary flow rate. A complete concentration-activity curve ($10^{-10}$ to $10^{-6}$M) is prepared for each substance. The two most important measurement parameters are: (1) CBF: coronary blood flow (in ml/min)—the velocity of blood flow through the coronary arteries and (2) dp/dt: rate of increase in left ventricular pressure (in mmHg/sec), as a measurement of the contractility force of the heart; this value is given as the % maximal variation from the initial value (Δ %) per dosage administered.

C. Haemodynamic parameters in the narcotized dog:

The 4 most important measurement parameters (with the respective measurement units) of the haemodynamic experiment are: (1) CBF: coronary blood flow (in ml/min)—the velocity of blood flow through the coronary arteries; (2) HR: heart rate (in beats/min)—the heart frequency; (3) BP: blood pressure (in mm Hg)—the blood pressure; and (4) dp/dt: rate of increase in left ventricular pressure (in mm Hg/sec) as a measurement of the contractility force of the heart. The values are given as the % maximum variation from the initial value (Δ %) and the duration of this variation (t) per dosage administered.

There is thus obtained not only an overall picture of the activity of the substance, but also an estimation as to the potential selectivity for a specific part of the circulatory system in the entire organism. After the administration of an anaesthetic, the dog is intubated and respired artificially. Blood pH, pC$_2$O , pO$_2$ and haemoglobin are measured hourly with a blood-gas analyser. The blood pressure (systolic and diastolic) is measured with a probe in the aorta abdominalis. The heart freguency is recorded by means of a tachometer, which is disengaged from the pressure pulse. For the other measurements the heart must be firstly be opened in order that a probe can be inserted in the left ventricle (heart chamber) for the pressure measurements (dp/dt). The coronary blood flow is measured with a flowing probe in the left coronary artery (descendens).

The results obtained in these tests are compiled in the following Table:

TABLE

| Compound | A<br>IC$_{50}$<br>[M] | B<br>CBF<br>IC$_{50}$<br>[M] | dp/dt<br>Δ % | C<br>CBF<br>Δ % | HR<br>Δ % | BP<br>Δ % | dp/dt<br>Δ % | Dosage<br>mg/kg i.v. |
|---|---|---|---|---|---|---|---|---|
| A | $1.3 \cdot 10^{-7}$ | $4.7 \cdot 10^{-8}$ | 250 | 86 | −7 | −22 | 25 | 0.3 |
| B | $6.3 \cdot 10^{-7}$ | $5.0 \cdot 10^{-8}$ | 216 | 36 | 0 | −6 | 8 | 0.3 |
| C | $2.1 \cdot 10^{-7}$ | $1.7 \cdot 10^{-8}$ | 192 | 62 | −9 | −16 | 15 | 0.3 |
| D | $3.2 \cdot 10^{-8}$ | $1.1 \cdot 10^{-9}$ | 162 | 22 | −25 | −21 | 6 | 0.03 |
| E | $1.0 \cdot 10^{-6}$ | $1.0 \cdot 10^{-5}$ | 164 | 57 | 0 | −8 | 10 | 1 |
| F | $3.4 \cdot 10^{-8}$ | $2.8 \cdot 10^{-8}$ | 130 | 46 | −2 | −3 | 4 | 0.3 |
| G | $1.5 \cdot 10^{-7}$ | $1.8 \cdot 10^{-9}$ | 237 | 96 | −15 | −20 | 11 | 0.3 |
| H | $2.8 \cdot 10^{-8}$ | $2.4 \cdot 10^{-9}$ | 222 | 146 | −41 | −28 | 25 | 0.3 |
| I | $1.0 \cdot 10^{-7}$ | $2.2 \cdot 10^{-8}$ | 124 | 82 | −9 | −14 | 18 | 0.3 |

A = [1S,2S]—2-[2-[[3-(2-Benzimidazolyl)propyl]methylamino]-ethyl]-6-fluoro-1,2,3,4-tetrahydro-1-isopropyl-2-naphthyl methoxyacetate
B = [1S,2S]—2-[2-[[7-(2-benzimidazolyl)heptyl]methylamino]-ethyl]-6-fluoro-1,2,3,4-tetrahydro-1-isopropyl-2-naphthalenol
C = [1S,2S]—6-Fluoro-1,2,3,4-tetrahydro-1-isopropyl-2-[2-[methyl-[5-(1-methyl-2-benzimidazolyl)pentyl]amino]-ethyl]-2-naphthyl butylcarbamate
D = [1S,2S]—6-Fluoro-1,2,3,4-tetrahydro-1-isopropyl-2-[2-[methyl-[6-(2-oxo-1-benzimidazolinyl)hexyl]amino]-ethyl]-2-naphthyl methoxyacetate
E = [1S,2S]—2-[2-[[3-(2-Benzimidazolyl)propyl]methyl-N—oxidoamino]ethyl]-6-fluoro-1,2,3,4-tetrahydro-1-isopropyl-2-naphthyl methoxyacetate
F = [1S,2S]—2-[2-[[7-(1-Dodecyl-2-benzimidazolyl)heptyl]-methylamino]ethyl]-6-fluoro-1,2,3,4-tetrahydro-1-isopropyl-2-naphthyl methoxyacetate
G = [1S,2S]—2-6-Fluoro-1,2,3,4-tetrahydro-1-isopropyl-2-[2-[[3-(1-methyl-4,5-diphenylimidazol-2-yl)propyl]methyl-amino]ethyl]-2-naphthyl methoxyacetate
H = [1S,2S]—2-[2-[[5-(2-Benzthiazolyl)pentyl]methylamino]-ethyl]-6-fluoro-1,2,3,4-tetrahydro-1-isopropyl-2-naphthyl methoxyacetate
I = [1S,2S]—6-Fluoro-1,2,3,4-tetrahydro-1-isopropyl-2-[2-[[4-[(2-benzimidazolyl)methyl]benzyl]methylamino]-ethyl]-2-naphthyl methoxyacetate In the Table above, the IC$_{50}$ of compound A in Test A is given as 1.3·10$^{-7}$. This means 1.3×10$^{-7}$. All other numbers which are similarly written have corresponding meanings. Thus 4.7·10$^{-8}$ means 4.7×10$^{-8}$.

The compounds of formula I can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. The administration can, however, also be carried out rectally, e.g. in the form of suppositories, or parenterally, e.g. in the form of injection solutions.

For the manufacture of tablets, coated tablets, dragees and hard gelatine capsules the compounds of formula I can be processed with pharmaceutically inert excipients. A pharmaceutically inert excipient includes inorganic or organic excipients or mixtures thereof. For tablets, dragees and hard gelatine capsules, excipients such as lactose, maize starch or derivatives thereof, talc, stearic acid or its salts etc. may be used.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerine, vegetable oils etc.

Suitable excipients for suppositories are e.g. natural or hardened oils, waxes, fats, semi-liquid or liquid polyols etc.

Moreover, the pharmaceutical preparations can contain preserving agents, solubilizers, stabilizing agents, wetting agents, emulsifying agents, sweetening agents, colouring agents, flavouring agents, salts for varying the osmotic pressure, buffers, coating agents or antioxidants. They can also contain still other therapeutically valuable substances.

The invention also relates to pharmaceutical compositions for the treatment or prevention of angina pectoris, ischaemia, arrhythmias, high blood pressure and cardiac insufficiency which comprise a compound of formula I and a pharmaceutically inert, inorganic or organic excipient.

The invention also relates to a method for treating or preventing angina pectoris, ischaemia, arrhythmias, high blood pressure and cardiac insufficiency which comprises administering an effective amount of a compound of formula I to a warm-blooded animal in need of such treatment.

In accordance with the invention compounds of formula I can be used in the control or prevention of angina pectoris, ischaemia, arrhythmias, high blood pressure and cardiac insufficiency by administering an effective amount of a compound of formula I to a warm-blooded animal in need of such treatment. The dosage can vary within wide limits and will, of course, be adjusted to the individual requirements in each particular case. In general, in the case of oral administration a daily dosage of about 25 to 150 mg of a compound of formula I should be appropriate, whereby, however, the upper limit just given can also be exceeded when this is shown to be indicated.

The following Examples are intended to illustrate the invention, but they are not intended to be limiting in any manner. All temperatures are given in degrees Celsius.

EXAMPLE 1

A mixture of 5.4 g (28.7 mmol) of 2-[3-(methylamino)propyl]benzimidazole, 11.4 g (28.7 mmol) of 2-(6-fluoro-1,2,3,4-tetrahydro-2-hydroxy-1α-isopropyl-2β-naphthyl)ethyl p-toluenesulphonate and 3.74 g (28.7 mmol) of Hünig base is heated to 120° for 30 minutes. The mixture is thereupon poured into ice-water and extracted with methylene chloride. After drying the organic phase over magnesium sulphate the solvent is evaporated and the residue is chromatographed on silica gel with a 6:1 mixture of methylene chloride and methanol as the elution agent. There are thus obtained 6.2 g (49%) of [1S,2S]-2-[2-[[3-(2-benzimidazolyl)propyl]methylamino]ethyl]-6-fluoro-1,2,3,4-tetrahydro-1-isopropyl-2-naphthalenol, [α]$_{589}^{20}$=+41.2° (c=0.8%; methanol).

The 2-[3-(methylamino)propyl]benzimidazole used as the starting material was prepared as follows:

22.8 g (91 mmol) of 4-[1-(benzyloxy)-N-methylformamido]butyric acid are dissolved in 200 ml of tetrahydrofuran. The mixture is cooled and 13 ml (128 mmol) of triethylamine and 12 ml (91.5 mmol) of isobutyl chloroformate are added dropwise thereto at −15°. After 2.5 hours 10.3 g (95 mmol) of o-phenylenediamine in 85 ml of tetrahydrofuran are added at −10° within 30 minutes. After stirring at room temperature for 1 hour the solvent is evaporated under reduced pressure. Thereupon, water is added and the mixture is extracted with ethyl acetate. The organic phase is washed with saturated aqeuous sodium bicarbonate solution and saturated aqueous sodium chloride solution. After drying over magnesium sulphate and evaporation of the solvent there are obtained 27.05 g of a product which is chromatographed on silica gel with ethyl acetate as the elution agent. There are thus obtained 20.1 g (71%) of benzyl [3-[(2-aminophenyl)carbamoyl]propyl]methylcarbamate.

MS: M+ 341.

20.1 g (59 mmol) of benzyl [3-[(2-aminophenyl)carbamoyl]propyl]methylcarbamate are dissolved in 450 ml of toluene and treated with 7 g (37 mmol) of p-toluenesulphonic acid. The reaction mixture is thereafter heated to reflux for 2 hours, whereby the water formed is removed from the reaction mixture by means of a water separator. After evaporation and dissolution of the residue in ethyl acetate the solution is washed twice with saturated aqueous sodium bicarbonate solution and twice with saturated aqueous soiium chloride solution. The organic phase is dried over magnesium sulphate and evaporated. Chromatography of the crude product on silica gel with ethyl acetate as the elution agent yields 11 g (58%) of benzyl [3-(2-benzimidazolyl)propyl]methylcarbamate, m.p. 83°–86°.

11.0 g (34 mmol) of benzyl [3-(2-benzimidazolyl)propyl]methylcarbamate are reduced with hydrogen in 150 ml of methanol in the presence of 2.5 g of palladium-on-carbon (5%) as the catalyst. There are thus obtained 5.45 g (85%) of 2-[3-(methylamino)propyl]benzimidazole, m.p. 134°–136°.

EXAMPLE 2

6.2 g (14.6 mmol) of [1S,2S]-2-[2-[[3-(2-benzimidazolyl)propyl]methylamino]ethyl]-6-fluoro-1,2,3,4-tetrahydro-1-isopropyl-2-naphthalenol are dissolved in 50 ml of chloroform. 2.5 ml (15 mmol) of N-ethyldiisopropylamine and 5 ml (55 mmol) of methoxyacetyl chloride are added thereto at 0°. The reaction mixture is stirred at room temperature overnight and thereafter treated with 100 ml of 1N sodium hydroxide solution and extracted with chloroform. After drying over magnesium sulphate and evaporation of the solvent the residue is chromatographed on silica gel with a 6:1 mixture of methylene chloride and methanol. There are thus obtained 6.2 g of an oil which are dissolved in 30 ml of ethanol and treated with 15 ml of ether saturated with hydrochloric acid. Thereupon, the reaction mixture is evaporated and the residue is crystallized from ethanol/diethyl ether. There are thus obtained 5.4 g (65%) of [1S,2S]-2-[2-[[3-(2-benzimidazolyl)propyl]methylamino]ethyl]-6-fluoro-1,2,3,4-tetrahydro-1-isopropyl-2-naphthyl methoxyacetate dihydrochloride, m.p. 128°.

EXAMPLE 3

A mixture of 4.2 g (10.35 mmol) of 2-(6-fluoro-1,2,3,4-tetrahydro-2-hydroxy-1α-isopropyl-2β-naphthyl)ethyl p-toluenesulphonate and 4.5 g (20.7 mmol) of 2-[5-(methylamino)pentyl]benzimidazole is heated to 100° for 30 minutes. Thereafter there are added firstly 100 ml of chloroform, then, after cooling, 100 ml of ether and finally 100 ml of 1N aqueous hydrochloric acid. After stirring for 30 minutes the reaction mixture is made basic with concentrated aqueous sodium hydroxide solution and the organic phase is decanted off, dried and evaporated. After chromatography on silica gel with a 6:1 mixture of methylene chloride and methanol there are obtained 2.7 g (58.2%) of [1S,2S]-2-[2-[[5-(2-benzimidazolyl)pentyl]methylamino]ethyl]-6-fluoro-1,2,3,4-tetrahydro-1-isopropyl-2-naphthalenol, $[\alpha]_{589}^{20} = +36.8°$ (c=0.25; methanol).

EXAMPLE 4

6 g (13.2 mmol) of [1S,2S]-2-[2-[[5-(2-benzimidazolyl)pentyl]methylamino]ethyl]-6-fluoro-1,2,3,4-tetrahydro-1-isopropyl-2-naphthalenol, 20 ml of methoxyacetic anhydride and 1.05 g (13.3 mmol) of pyridine are heated to 0° while stirring. After 2 hours the mixture is cooled and treated with 500 ml of 3N sodium hydroxide solution and 500 ml of methylene chloride and stirred vigorously. The organic phase is dried over magnesium sulphate and evaporated. The residue is dissolved in ethanol and treated with ether saturated with hydrochloric acid. After evaporation and crystallization from ethanol/ether there are obtained 6.2 g (78.5%) of [1S,2S]-2-[2-[[5-(2-benzimidazolyl)pentyl]methylamino]ethyl]-6-fluoro-1,2,3,4-tetrahydro-1-isopropyl-2-naphthyl methoxyacetate dihydrochloride, m.p. 196°-198°.

EXAMPLE 5

The following compounds were prepared in an analogous manner to that described in Examples 1 and 3:
starting from 2-(6-fluoro-1,2,3,4-tetrahydro-2-hydroxy-1α-isopropyl-2β-naphthyl)ethyl p-toluenesulphonate and 2-[4-(methylamino)butyl]benzimidazole the [1S,2S]-2-[2-[[4-(2-benzimidazolyl)butyl]methylamino]ethyl]-6-fluoro-1,2,3,4-tetrahydro-1-isopropyl-2-naphthalenol, MS: M+ 437;
starting from 2-(6-fluoro-1,2,3,4-tetrahydro-2-hydroxy-1α-isopropyl-2β-naphthyl)ethyl p-toluenesulphonate and 2-[7-(methylamino)heptyl]benzimidazole the [1S,2S]-2-[2-[[7-(2-benzimidazolyl)heptyl]methylamino]ethyl]-6-fluoro-1,2,3,4-tetrahydro-1-isopropyl-2-naphthalenol dihydrochloride, $[\alpha]_{589}^{20} = +32.9°$ (c=1%; methanol);
starting from 2-(6-fluoro-1,2,3,4-tetrahydro-2-hydroxy-1α-isopropyl-2β-naphthyl)ethyl p-toluenesulphonate and 2-[11-(methylamino)undecyl]benzimidazole the [1S,2S]-2-[2-[[11-(2-benzimidazolyl)undecyl]methylamino]ethyl]-6-fluoro-1,2,3,4-tetrahydro-1-isopropyl-2-naphthalenol;
starting from 2-(6-fluoro-1,2,3,4-tetrahydro-2-hydroxy-1α-isopropyl-2β-naphthyl)ethyl p-toluenesulphonate and 5,6-dimethyl-2-[7-(methylamino)heptyl]benzimidazole the [1S,2S]-2-[2-[[7-(5,6-dimethyl-2-benzimidazolyl)heptyl]methylamino]ethyl]-6-fluoro-1,2,3,4-tetrahydro-1-isopropyl-2-naphthalenol, $[\alpha]_{589}^{20} = +33.6°$ (c=0.5%; methanol);
starting from 2-(6-fluoro-1,2,3,4-tetrahydro-2-hydroxy-1α-isopropyl-2β-naphthyl)ethyl p-toluenesulphonate and 2-[5-(dodecylamino)pentyl]benzimidazole the [1S,2S]-2-[2-[[5-(2-benzimidazolyl)pentyl]-dodecylamino]ethyl]-6-fluoro-1,2,3,4-tetrahydro-1-isopropyl-2-naphthalenol, MS: M+ 606;
starting from 2-(6-fluoro-1,2,3,4-tetrahydro-2-hydroxy-1α-isopropyl-2β-naphthyl)ethyl p-toluenesulphonate and 2-[7-(methylamino)heptyl]-1H-imidazo[4,5-c]pyridine the [1S,2S]-6-fluoro-1,2,3,4-tetrahydro-1-isopropyl-2-[2-[[7-(1H-imidazo[4,5-c]pyridin-2-yl)heptyl]methylamino]ethyl]-2-naphthalenol, MS: M+ 480.

The benzimidazole derivatives used as the starting materials were prepared in an analogous manner to that described in Example 1.

EXAMPLE 6

The following compounds were prepared by methoxy-acetylating the corresponding hydroxy derivatives in an analogous manner to that described in Examples 2 and 4:
[1S,2S]-2-[2-[[4-(2-Benzimidazolyl)butyl]methylamino]ethyl]-6-fluoro-1,2,3,4-tetrahydro-1-isopropyl-2-naphthyl methoxyacetate dihydrochloride, $[\alpha]_{589}^{20} = +28.6°$ (c=1%; methanol);
[1S,2S]-2-[2-[[7-(2-benzimidazolyl)heptyl]methylamino]ethyl]-6-fluoro-1,2,3,4-tetrahydro-1-isopropyl-2-naphthyl methoxyacetate dihydrochloride, $[\alpha]_{589}^{20} = +25.4°$ (c=1%; methanol);
[1S,2S]-2-[2-[[11-(2-benzimidazolyl)undecyl]methylamino]ethyl]-6-fluoro-1,2,3,4-tetrahydro-1-isopropyl-2-naphthyl methoxyacetate dihydrochloride. $[\alpha]_{589}^{20} = +23.7°$ (c=1%; methanol);
[1S,2S]-2-[2-[[7-(5,6-dimethyl-2-benzimidazolyl)heptyl]methylamino]ethyl]-6-fluoro-1,2,3,4-tetrahydro-1-isopropyl-2-naphthyl methoxyacetate hydrochloride, (1:1.85), $[\alpha]_{589}^{20} = +26.5°$ (c=1%; methanol);
[1S,2S]-2-[2755 -[[5-(2-benzimidazolyl)pentyl]-dodecylamino]ethyl]-6-fluoro-1,2,3,4-tetrahydro-1-isopropyl-2-naphthyl methoxyacetate dihydrochloride, $[\alpha]_{589}^{20} = +22.0°$ (c=0.25%; methanol);
[1S,2S]-6-fluoro-1,2,3,4-tetrahydro-1-isopropyl-2-[2-[[7-(1H-imidazo[4,5-c]pyridin-2-yl)heptyl]methylamino]ethyl]-2-naphthyl methoxyacetate dihydrochloride, m.p. 112°-115°.

EXAMPLE 7

0.79 g (3.8 mmol) of 2-[3-(methylamino)propyl]benzthiazole, 1.54 g (3.8 mmol) of 2-(6-fluoro-1,2,3,4-tetrahydro-2-hydroxy-1α-isopropyl-2β-naphthyl)ethyl p-toluenesulphonate and 0.49 g (3.8 mmol) of Hünig base are stirred at 120° for 2.5 hours. After cooling and dissolution of the precipitate with a small amount of methylene chloride the reaction solution is chromatographed on silica gel with a 12:1 mixture of methylene chloride and methanol. There are thus obtained 1.12 g (76%) of [1S,2S]-2-[2-[[3-(2-benzthiazolyl)propyl]methylamino]ethyl]-6-fluoro-1,2,3,4-tetrahydro-1-isopropyl-2-naphthalenol, MS: M+ 440.

The following compounds were prepared in an analogous manner to that described above:
starting from 2-(6-fluoro-1,2,3,4-tetrahydro-2-hydroxy-1α-isopropyl-2β-naphthyl)ethyl p-toluenesulphonate and 2-[5-(methylamino)pentyl]benzthiazole the [1S,2S]-2-[2-[[5-(2-benzthiazolyl)pentyl]methylamino]ethyl]-6-fluoro-1,2,3,4-tetrahydro-1-isopropyl-2β-naphthalenol, MS: M+ 468;
starting from 2-(6-fluoro-1,2,3,4-tetrahydro-2-hydroxy-1α-isopropyl-28-naphthyl)ethyl p-toluenesulphonate and 2-[7-(methylamino)heptyl]benzthiazole the [1S,2S]-2-[2-[[7-(2-benzthiazolyl)heptyl]methylamino]ethyl]- 6-fluoro-1,2,3,4-tetrahydro-1-isopropyl-2-naphthalenol, MS: M+ 496.

The 2-[3-(methylamino)propyl]benzthiazole used as the starting material was prepared as follows:

5.0 g (19.9 mmol) of 4-[1-(benzyloxy)-N-methylformamido]butyric acid are dissolved in 175 ml of tetrahydrofuran. To the solution, cooled to −20°, are added 2.95 ml (2.1 g; 24 mmol) of triethylamine and 2.95 ml (22 mmol) of isobutyl chloroformate. The reaction mixture is thereafter stirred at this temperature for 1 hour. 2.45 g (19.6 mmol) of 2-aminothiophenol are then added and the reaction mixture is stirred at room temperature for 20 hours. Thereupon, 250 ml of water are added and the mixture is extracted with ethyl acetate. The organic phase is dried over magnesium sulphate and evaporated under reduced pressure. After chromatography on silica gel using a 1:1 mixture of ethyl acetate and hexane there are obtained 1.7 g (25.1%) of benzyl [3-(2-benzthiazolyl)propyl]methylcarbamate as an oil, MS: M+ 340.

1.7 g (4.99 mmol) of benzyl [3-(2-benzthiazolyl)propyl]methylcarbamate are dissolved at 0° in 40% hydrogen bromide in acetic acid and stirred at room temperature for 20 hours. Thereupon, 60 ml of ether are added and, after 1.5 hours, the precipitate formed is filtered off. After washing the crystalline precipitate with ether and drying there are obtained 1.71 g (93.1%) of 2-[3-(methylamino)propyl]benzthiazole dihydrobromide, m.p. 196°-197°.

The following compounds were prepared in an analogous manner to that described above:
2-[5-(methylamino)pentyl]benzthiazole, MS: M+ 234;
2-[7-(methylamino)heptyl]benzthiazole, MS: M+ 262.

EXAMPLE 8

1.12 g (2.54 mmol) of [1S,2S]-2-[2-[[3-(2-benzthiazolyl)propyl]methylamino]ethyl]-6-fluoro-1,2,3,4-tetrahydro-1-isopropyl-2-naphthalenol are dissolved in 0.2 g of pyridine. 5 ml of methoxyacetic anhydride are added thereto. The reaction mixture is heated to 60° for 2 hours. Thereafter, 100 ml of 1N sodium hydroxide solution are added thereto at 0° and the mixture is extracted with 100 ml of ethyl acetate. The organic phase is dried with magnesium sulphate, filtered and evaporated under reduced pressure. The residue is chromatographed on silica gel using a 30:1 mixture of methylene chloride and methanol. There is thus obtained 0.9 g of an oily product which is dissolved in ethyl acetate and treated with ether saturated with hydrochloric acid. After evaporation to 20 ml, 40 ml of ether are added and the reaction mixture is stirred for 1 hour. The separated precipitate is filtered off and dried. There is thus obtained 0.9 g (64.5%) of [1S,2S]-2-[2-[[3-(2-benzthiazolyl)propyl]methylamino]ethyl]-6-fluoro-1,2,3,4-tetrahydro-1-isopropyl-2-naphthyl methoxyacetate dihydrochloride, m.p. 130°-134°.

The following compounds were prepared by methoxy-acetylating the corresponding hydroxy derivatives in an analogous manner to that described above:
[1S,2S]-2-[2-[[5-(2-Benzthiazolyl)pentyl]methylamino]ethyl]-6-fluoro-1,2,3,4-tetrahydro-1-isopropyl-2-naphthyl methoxyacetate hydrochloride (5:8), $[\alpha]_{589}^{20} = +27.4°$ (c=0.5%; methanol);
[1S,2S]-2-[2-[[7-(2-benzthiazolyl)heptyl]methylamino]ethyl]-6-fluoro-1,2,3,4-tetrahydro-1-isopropyl-2-naphthyl methoxyacetate hydrochloride (4:5), $[\alpha]_{589}^{20} = +25.8°$ (c=1%; methanol).

EXAMPLE 9

In an analogous manner to that described in Examples 1 and 4, starting from (S)-6-[1-(benzyloxy)-N-methylformamido]heptanoic acid via [1S,2S]-2-[2-[[(S)-5-(2-benzimidazolyl)-1-methylpentyl]methylamino]ethyl]-6-fluoro-1,2,3,4-tetrahydro-1-isopropyl-2-naphthalenol there was prepared [1S,2S]-2-[2-[[(S)-5-(2-benzimidazolyl)-1-methylpentyl]methylamino]ethyl]-6-fluoro-1,2,3,4-tetrahydro-1-isopropyl-2-naphthyl methoxyacetate dihydrochloride, $[\alpha]_{589}^{20} = +20.0°$ (c=0.7%; methanol).

The (S)-6-[1-(benzyloxy)-N-methylformamido]heptanoic acid used as the starting material was prepared as follows:

200 g (1.39 mol) of 6-oxoheptanoic acid are dissolved in 1.2 l of methylene chloride. 14 ml of concentrated sulphuric acid are added thereto at −20°. 0.6 l (6.3 mol) of isobutylene is then condensed at −40° and thereupon left to distil into the reaction flask. Thereafter, the reaction mixture is left to react for 6 days at room temperature under the reflux of the reagent. Thereafter, one liter of saturated aqueous sodium bicarbonate solution is added thereto while stirring. The aqueous phase is extracted with methylene chloride. The combined organic phases are dried over magnesium sulphate and evaporated under reduced pressure. There are thus obtained 268.0 g (1.338 mol; 96.4%) of tert.-butyl 6-oxoheptanoate, which are heated to reflux for 12 hours together with 162.1 g (1.338 mol) of (S)-(−)-1-phenylethylamine and 5.8 g (30.5 mmol) of p-toluenesulphonic acid in 1.9 l of toluene with the simultaneous separation of water. After evaporation of the solvent there are obtained 395.5 g (1.3 mol; 97.4%) of tert.butyl (E/Z)-6-[[(R)-α-methylbenzyl]imino]heptanoate which are dissolved in 7 l of methanol. 43 g of Raney-nickel are added thereto and the mixture is hydrogenated at 10 bar for 24 hours. Thereafter, the mixture is filtered and the solution is evaporated. The resulting 378.5 g of oil are dissolved in 1.1 l of ethylacetate and treated at 0° with 130 ml of 10N ethanolic hydrochloric acid. After stirring at 0° for 1 hour the crystals formed are filtered off and dried. By three-fold recrystallization of the resulting 282 g of crystals from ethyl acetate there are obtained 172.7 g (38.9%) of tert.butyl (S)-6-[[(S)-α-methylbenzyl]amino]hexanoate hydrochloride, m.p. 154°-156°.

160 g (0.648 mol) of the above hydrochloride are dissolved in 2.4 l of ethanol and hydrogenated at 10 bar in the presence of 20 g of palladium-on-carbon (5%). After filtering off the catalyst the solvent is evaporated and the residue is crystallized from 560 ml of ethyl acetate and 240 ml of hexane. There are thus obtained 101 g (90.8%) of tert.-butyl (S)-6-aminoheptanoate hydrochloride, m.p. 107°–109°.

89 g (374 mmol) of tert.butyl (S)-6-aminoheptanoate hydrochloride are dissolved in 1.3 l of methylene chloride. The solution is saturated with hydrogen chloride and heated to reflux for 4 hours. After filtering off and drying the precipitate formed there are obtained 60.8 g (89.5%) of (S)-6-aminoheptanoic acid hydrochloride, m.p. 157°–160°.

To 30 g (166 mmol) of (S)-6-aminoheptanoic acid hydrochloride in 57 ml of water are added 57 ml of 4N aqueous sodium hydroxide solution and thereafter dropwise simultaneously at 10° 92 ml of 4N aqueous sodium hydroxide solution and 42 ml (294 mol) of benzyl chloroformate so that the pH value always lies between 10 and 12. After the precipitation of the product the mixture is stirred at 0° for a further 2 hours. Thereafter, 300 ml of water are added and the reaction mixture is extracted with ether. The aqueous phase is then acidified with 20 ml of concentrated hydrochloric acid and extracted with methylene chloride. The methylene chloride phase is dried over magnesium sulphate and evaporated. The crystals obtained are recrystallized from chloroform/hexane, whereby there are obtained 33.1 g (72%) of (S)-6-[1-(benzyloxy)formamido]heptanoic acid, m.p. 82°–83°.

6.5 g (23 mmol) of (S)-6-[1-(benzyloxy)formamido]-heptanoic acid are added to a suspension of 3.05 g of 55% sodium hydride (70 mmol) in 200 ml of dimethylformamide and the mixture is left to react at 40° for 30 minutes. Thereafter, 13 g (90 mmol) of methyl iodide are added dropwise and the reaction mixture is heated to 70° for 1 hour. After evaporation of the solvent 120 ml of 1N agueous sodium hydroxide solution and 120 ml of ethanol are added and the reaction mixture is heated to reflux for 30 minutes. Thereafter, the mixture is evaporated to half, 100 ml of saturated aqueous sodium bicarbonate solution are added and the mixture is extracted with ethyl acetate. The aqueous phase is acidified and extracted with methylene chloride. The organic phase is dried over magnesium sulphate and evaporated. The residue (5 g) is chromatographed on silica gel with a 12:1 mixture of methylene chloride and methanol, whereby there are obtained 3.5 g (52.2%) of (S)-6-[1-(benzyloxy)-N-methylformamido]heptanoic acid, MS: M+ 293.

EXAMPLE 10

A mixture of 1.4 g (3.33 mmol) of 2-[[1S,2S]-6-fluoro-1,2,3,4-tetrahydro-1-isopropyl-2-methoxy-2-naphthyl]ethyl p-toluenesulphonate and 1.63 g (6.66 mmol) of 2-[7-(methylamino)heptyl]benzimidazole is heated to 100° for 30 minutes. The mixture is thereafter poured into 100 ml of water and extracted with 100 ml of ethyl acetate. The organic phase is dried over magnesium sulphate and evaporated under reduced pressure, and the residue is chromatographed on silica gel with a 6:1 mixture of methylene chloride and methanol. There is thus obtained a yellowish oil (1 g) which is dissolved in 20 ml of ethanol and treated with 2 ml of ether saturated with hydrochloric acid. The mixture is then evaporated under reduced pressure and the residue is crystallized from ethyl acetate/ethanol/ether and dried, whereby there is obtained 0.7 g (37.2% of [1S,2S]-2-[2-[[7-(2-benzimidazolyl)heptyl]methylamino]ethyl]-6-fluoro-1,2,3,4-tetrahydro-1-isopropyl-2-methoxynaphthalenol dihydrochloride, m.p. 179°–181°.

The 2-[[1S,2S]-6-fluoro-1,2,3,4-tetrahydro-1-isopropyl-2-methyoxy-2-naphthyl]ethyl p-toluenesulphonate used as the starting material was prepared as follows:

A mixture of 5.04 g (20 mmol) of 6997 -fluoro-1,2,3,4-tetrahydro-2-isopropyl-2-hydroxy-1α-isopropyl-2β-naphthylethanol, 6.13 g (22 mmol) of triphenylchloromethane and 50 ml of pyridine is stirred at room temperature for 20 hours. The reaction mixture is thereafter poured into 500 ml of ice-water and extracted with 400 ml of ether. The ether extracts are washed with 400 ml of 1N aqueous hydrochloric acid, 400 ml of saturated aqueous sodium bicarbonate solution and 400 ml of water. After drying over magnesium sulphate the ether is evaporated under reduced pressure. There are obtained 8.25 g (83%) of [1S,2S]-6-fluoro-1,2,3,4-tetrahydro-1-isopropyl-2-[2-(trityloxy)ethyl]-2-naphthalenol. 8 g (16.2 mmol) of this compound are dissolved in 300 ml of tetrahydrofuran and treated at −20° with 35.6 mmol of freshly prepared lithium diisopropylamide. Thereafter, 9.2 g (64.8 mmol) of methyl iodide are added and the reaction mixture is stirred at room temperature for 20 hours. The reaction mixture is poured into ice-water and extracted with methylene chloride. The organic phase is dried over magnesium sulphate and the solvent is evaporated under reduced pressure. After chromatography on silica gel using a 1:2 mixture of methylene chloride and hexane and recrystallization from hexane there are obtained 4.15 g (54.7%) of [1S,2S]-6-fluoro-1,2,3,4-tetrahydro-1-isopropyl-2-methoxy-2-[2-trityloxy)ethyl]naphthalenol, m.p. 132°–134°.

4.15 g (8.16 mmol) of the above compound are left to stand at 0° for 2 hours with 15 ml of ether saturated with hydrochloric acid. After evaporation of the solvent and chromatography of the residue on silica gel using a 1:2 mixture of ethyl acetate and hexane there is obtained 1.0 g (47%) of [1S,2S]-6-fluoro-1,2,3,4-tetrahydro-1-isopropyl-2-methoxy-2-naphthylethanol, $[\alpha]_{589}^{20}= +65.6°$ (c=0.25%; methanol).

0.98 g (3.7 mmol) of [1S,2S]-6-fluoro-1,2,3,4-tetrahydro-1-isopropyl-2-methoxy-2-naphthylethanol is dissolved in 6 ml of pyridine and left to react at 0° for 1 hour with 1.06 g (5.6 mmol) of toluene-4-sulphochloride. The reaction mixture is thereafter poured into 100 ml of water and extracted with 200 ml of ether. The ether extract is washed with 100 ml of 1N aqueous hydrochloric acid, 100 ml of saturated aqueous sodium bicarbonate solution and 100 ml of water. After drying the ethereal solution over magnesium sulphate and evaporation of the solvent there are obtained 1.50 g (97.4%) of 2-[[1S,2S]-6-fluoro-1,2,3,4-tetrahydro-1-isopropyl-2-methoxy-2-naphthyl]ethyl p-toluenephonate, $[\alpha]_{589}^{20}= +42.6$ (c=0.5%; methanol).

EXAMPLE 11

2.0 g (4.43 mmol) of [1S,2S]-2-[2-[[5-(2-benzimidazolyl)phenyl]methylamino]ethyl ]-6-fluoro-1,2,3,4-tetrahydro-1-isopropyl-2-naphthalenol dissolved in 30 ml of tetrahydrofuran are added to a suspension of 436 mg (10 mmol) of 55% sodium hydride in 20 ml of tetrahydrofuran. After stirring at room temperature for 45 minutes 1.42 g (10 mmol) of methyl iodide are added thereto. After a further hour, water and methylene chloride are added and the reaction mixture is shaken vigorously. The organic phase is dried over magnesium sulphate and evaporated. The residue is chromatographed on silica gel with a 6:1 mixture of methylene chloride and methanol, whereby there are obtained 1.2 g (60%) of [1S,2S]-6-fluoro-1,2,3,4-tetrahydro-1-isopropyl-2-[2-[methyl-5-(1-methyl-2-benzimidazolyl)pentyl-]amino]ethyl]-2-naphthalenol, MS: M+ 465.

[1S,2S]-2-[2-[[7-(1-Dodecyl-2-benzimidazolyl)heptyl]methylamino]ethyl]-6-fluoro-1,2,3,4-tetrahydro-1-isopropyl-2-naphthalenol was prepared in analogous manner to that described above by reaction with dodecyl iodide.

EXAMPLE 12

A mixture of 1.2 g (2.58 mmol) of [1S,2S]-6-fluoro-1,2,3,4-tetrahydro-1-isopropyl-2-[2-[methyl-[5-(1-methyl-2-benzimidazolyl)pentyl]amino]ethyl]-2-naphthalenol, 206 mg (2.6 mmol) of pyridine and 4 ml of methoxyacetic anhydride is heated to 70° for 2 hours. Thereafter, 100 ml of 3N aqueous sodium hydroxide solution are added thereto and the mixture is extracted with 100 ml of methylene chloride. The organic phase is dried over magnesium sulphate and evaporated. The product is chromatographed on silica gel using a 15:1 mixture of methylene chloride and methanol. The resulting 550 mg of oil are dissolved in 50 ml of ethyl acetate and treated with 1 ml of ether saturated with hydrochloric acid. After evaporation of the solvent the residue is crystallized from ethyl acetate/ether, whereby there are obtained 600 mg (41%) of [1S,2S]-6-fluoro-1,2,3,4-tetrahydro-1-isopropyl-2-[2-[methyl-[5-(1-methyl-2-benzimidazolyl)pentyl]amino]ethyl]-2-naphthyl methoxyacetate dihydrochloride, m.p. 203°–205°.

[1S,2S]-2-[2-[[7-(1-Dodecyl-2-benzimidazolyl)heptyl]methylamino]ethyl]-6-fluoro-1,2,3,4-tetrahydro-1-isopropyl-2-naphthyl methoxyacetate dihydrochloride, $[\alpha]_{589}^{20} = +20.4°$ (c=0.9%; methanol), was prepared in an anaoogous manner to that described above.

EXAMPLE 13

0.425 g (1 mmol) of [1S,2S]-2-[2-[[3-(2-benzimidazolyl)propyl]methylamino]ethyl]-6-fluoro-1,2,3,4-tetrahydro-1-isopropyl-2-naphthyl methoxyacetate is dissolved in 60 ml of methanol and subsequently treated with 10 ml of 6% hydrogen peroxide and 50 mg (0.15 mmol) of sodium tungstate. After stirring at room temperature for 20 hours 100 mg of platinum-on-carbon (5%) in 2 ml of water are added thereto and the mixture is stirred for a further hour. Thereupon, the mixture is filtered, the filtrate is concentrated, the residue is diluted with a small amount of methylene chloride and the mixture is chromatographed on silica gel with a 15:1 mixture of methylene chloride and methanol as the elution agent. There are thus obtained 0.18 g (35.2%) of a first diastereomer of [1S,2S]-2-[2-[[3-(2-benzimidazolyl)propyl]methyl-N -oxidoamino]ethyl]-6-fluoro-1,2,3,4-tetrahydro-1-isopropyl-2-naphthyl methoxyacetate with a $R_f$ value of 0.33, $[\alpha]_{589}^{20} = +39.4°$ (c=0.5%; methanol), and 0.276 g (54%) of a second diasteromer of the named compound with a $R_f$ value of 0.26 (methylene chloride/methanol 6:1), $[\alpha]_{589}^{20} = +34.8°$ (c=0.5%; methanol).

EXAMPLE 14

5.0 g (12.3 mmol) of 2-(6-fluoro-1,2,3,4-tetrahydro-2-hydroxy-1α-isopropyl-2β-naphthyl)ethyl p-toluenesulphonate and 4.0 g (24.6 mmol) of 2-methylaminobenzthiazole are heated to 120° for 30 minutes. Thereafter, 50 ml of a 12:1 mixture of methylene chloride and methanol are added and the reaction mixture is purified by column chromatography on silica gel using a 1:1 mixture of hexane and ethyl acetate as the elution agent. In this manner there are obtained 3.22 g (65.7%) of [1S,2S]-2-[2-[(2-benzthiazolyl)methylamino]ethyl]-6-fluoro-1,2,3,4-tetrahydro-1-isopropyl-2-naphthalenol, m.p. 102°–103°.

EXAMPLE 15

6.1 g (15 mmol) of [1S,2S]-2-(6-fluoro-1,2,3,4-tetrahydro-2-hydroxy-1-isopropyl-2-naphthyl)ethyl p-toluenesulphonate and 6.8 g (30 mmol) of 1-[2-(methylamino)ethyl]-2-benzimidazolinone hydrochloride are stirred at 130° for 4.5 hours in a mixture of 30 ml of dimethylformamide and 30 ml of N-ethyldiisopropylamine. The reaction mixture is poured into 600 ml of ice-water and extracted with 700 ml of methylene chloride. The extract is washed with water, dried over potassium carbonate and evaporated. The thus-obtained product is chromatographed on 150 g of silica gel with methylene chloride and 0–10% isopropanol as the elution agent, whereby 5.2 g (72%) of 1-[2-[[2-[[1S,2S]-6-fluoro-1,2,3,4-tetrahydro-2-hydroxy-1-isopropyl-2-naphthyl]ethyl]methylamino]ethyl]-2-benzimidazolinone are obtained as an oil.

The 1-[2-(methylamino)ethyl]-2-benzimidazolinone hydrochloride used as the starting material was prepared as follows:

93.8 ml (150 mmol) of a n-butyllithium solution (about 1.6M in hexane) are added dropwise at 0°–5° to 24.8 g (150 mmol) of 2-(N-benzyl-N-methylamino)ethanol dissolved in 250 ml of absolute tetrahydrofuran. After stirring at 0° for 15 minutes 11.7 ml (150 mmol) of methanesulphochloride in 50 ml of tetrahydrofuran are added dropwise at a temperature between 0° and 5° and the reaction mixture is stirred at 0° for 30 minutes.

5.8 g (133 mmol) of a 55% sodium hydride dispersion in mineral oil are washed oil-free with hexane and suspended in 40 ml of dimethylformamide. 23.1 g (132.5 mmol) of 1-(1-methylvinyl)benzimidazolin-2-one in 90 ml of dimethylformamide are subsequently added dropwise at room temperature and the reaction mixture is stirred for a further 15 minutes.

This reaction mixture is added dropwise at 0° to the reaction solution described above. Thereafter, the mixture is heated to 70° and stirred for 3 hours. The reaction mixture is subsequently poured into 1 l of ice-water and extracted with 600 ml of methylene chloride. The extract is washed with water, dried over potassium carbonate and evaporated. The thus-obtained product is chromatographed on 500 g of silica gel with methylene chloride and 0–5% isopropanol as the elution agent, whereby there are obtained 26.8 g (63%) of 1-(1-methylvinyl)-3-[2-(N-benzyl-N-methylamino)ethyl]-2-benzimidazolinone as an oil.

26.5 g (82.5 mmol) of the above-named compound are dissolved in 265 ml of ethanol, treated with 26.5 ml of concentrated aqueous hydrochloric acid while stirring and heated to reflux for 1 hour. After cooling the reaction mixture to 5°, 1-[2-(N-benzyl-N-methylamino)ethyl]-2-benzimidazolinone crystallizes out in the form of the hydrochloride, m.p. 107°–109°; yield 24.2 g (92%).

22.9 g (72 mmol) of 1-[2-(N-benzyl-N-methylamino)ethyl]-2-benzimidazolinone hydrochloride are dissolved in 250 ml of methanol, treated with 2.5 g of palladium-on-carbon (10%) and hydrogenated at room temperature for 90 minutes. The residue obtained after filtration and concentration is recrystallized from methanol/ether, whereby there are obtained 15.5 g (94%) of 1-[2-(methylamino)ethyl]-2-benzimidazolinone hydrochloride, m.p. 177°–180°.

EXAMPLE 16

4.57 g (10.7 mmol) of 1-[2-[[2-[[1S,2S]-6-fluoro-1,2,3,4-tetrahydro-2-hydroxy-1-isopropyl-2-naphthyl]ethyl]methylamino]ethyl]-2-benzimidazolinone are dissolved in 15 ml of methylene chloride, treated with 2.2 ml of pyridine and 7.0 g (43 mmol) of methoxyacetic anhydride and stirred at room temperature for 20 hours. Thereafter, the mixture is treated with 30 ml of 3N sodium hydroxide solution while cooling with ice and stirred at room temperature for 15 minutes. The reaction mixture is subsequently poured into 400 ml of ice-water and extracted with 600 ml of methylene chloride. The extract is washed with water, dried over potassium carbonate and concentrated. There are thus obtained 6.9 g of an oil (N,O-diacylated product) which are dissolved in 30 ml of methanol and treated at room temperature with 11.5 ml of 1N aqueous sodium hydroxide solution. After stirring for 30 minutes the mixture is poured into 400 ml of ice-water and extracted with 600 ml of methylene chloride. The extract is washed with water, dried over potassium carbonate, evaporated, treated with one equivalent of hydrochloric acid in methanol, again evaporated and finally recrystallized from methanol/ether. There are thus obtained 3.9 g (72%) of [1S,2S]-6-fluoro-1,2,3,4-tetrahydro-1-isopropyl-2-[2-[methyl-[2-(2-oxo-1-benzimidazolinyl)ethyl]amino]ethyl]-2-naphthyl methoxyacetate hydrochloride, m.p. 130°–133° (dec.); $[\alpha]_D^{20} = +26.0°$ (c=1%; methanol).

EXAMPLE 17

In analogy to Example 15, by reacting [1S,2S]-2-(6-fluoro-1,2,3,4-tetrahydro-2-hydroxy-1-isopropyl-2-naphthyl)ethyl p-toluenesulphonate with 1-[6-(methylamino)hexyl]-2-benzimidazolinone there was obtained 1-[6-[[2-[[1S,2S]-6-fluoro-1,2,3,4-tetrahydro-2-hydroxy-1-isopropyl- 2-naphthyl]ethyl]methylamino]hexyl]-2-benzimidazolinone as an oil.

The 1-[6-(methylamino)hexyl]-2-benzimidazolinone used as the starting material was prepared as follows:

17.6 g (150 mmol) of 6-amino-1-hexanol dissolved in 50 ml of methanol are added dropwise at room temperature to 32.7 g (150 mmol) of di-tert.-butyl dicarbonate in 100 ml of methanol. After stirring at room temperature for 4 hours the reaction mixture is evaporated, whereby there are obtained 36.6 g of tert.-butyl (6-hydroxyhexyl)carbamate as an oil which is used directly in the next step.

34.8 g of tert.-butyl (6-hydroxyhexyl)carbamate are dissolved in 250 ml of methylene chloride and treated at 0° with 24.0 ml (174 mmol) of triethylamine. Subsequently, 12.9 ml (166 mmol) of methanesulphochloride in 50 ml of methylene chloride are added dropwise at −60° within 15 minutes and the reaction mixture is subsequently stirred at −60° for 90 minutes. Thereafter, the reaction solution is poured into 600 ml of ice-water and extracted with 800 ml of methylene chloride. The organic extract is washed with water, dried over magnesium sulphate and evaporated. There are thus obtained 58.6 g of tert.-butyl [6-[(methylsulphonyl)oxy]hexyl]carbamate as an oil which is processed without purification.

5.9 g (135 mmol) of a 55% sodium hydride dispersion in mineral oil are washed oil-free with hexane and subsequently covered with 100 ml of dimethylformamide. To this suspension are added dropwise at room temperature 22.3 g (128 mmol) of 1-(1-methylvinyl)benzimidazolin-2-one in 100 ml of dimethylformamide. After stirring at room temperature for 2 hours 55.0 g of tert.-butyl [6-[(methylsulphonyl)oxy]hexyl]carbamate in 100 ml of dimethylformamide are added dropwise and the reaction mixture is stirred at room temperature for 18 hours. Thereafter, the reaction mixture is poured into 1 l of water and extracted with 750 ml of methylene chloride. The organic extract is washed with water, dried over potassium carbonate and evaporated. The thus-obtained residue is chromatographed on 950 g of silica gel with methylene chloride/hexane, methylene chloride and a 95:5 mixture of methylene chloride and isopropanol as the elution agent, whereby there are obtained 45.3 g of tert.-butyl [6-[3-(1-methylvinyl)-2-oxo-1-benzimidazolinyl]hexyl]carbamate as an oil.

5.3 g (121 mmol) of a 55% sodium hydride dispersion in mineral oil are washed oil-free with hexane and subsequently covered with 100 ml of dimethylformamide. To this suspension are added dropwise at room temperature 45.0 g (121 mmol) of tert.-butyl [6-[3-(1-methylvinyl)-2-oxo-1-benzimiaazolinyl]hexyl]carbamate and the reaction mixture is stirred at this temperature for 90 minutes. Subsequently, 9.0 ml (155 mmol) of methyl iodide in 50 ml of dimethylformamide are added dropwise at 10° and the reaction mixture is stirred at 10° for 1 hour and at room temperature for 16 hours. Thereafter, the reaction solution is poured into 800 ml of ice-water and extracted with 600 ml of methylene chloride. The extract is washed with water, dried over potassium carbonate and evaporated. The thus-obtained residue is chromatographed on 500 g of silica gel with hexane/ethyl acetate (4:1 and 1:1), whereby there are obtained 39.1 g of tert.-butyl methyl [6-[3-(1-methylvinyl)-2-oxo-1-benzimidazolinyl]hexyl]carbamate as an oil.

38.8 g (100 mmol) of the last-named compound are dissolved in 300 ml of absolute ethanol, treated while stirring with 40 ml of concentrated aqueous hydrochloric acid and heated to reflux for 75 minutes. After cooling to 40° the reaction mixture is concentrated under reduced pressure and poured into 500 ml of ice-water. The aqueous phase is adjusted to pH 8–9 by the addition of concentrated aqueous ammonia solution and extracted with 600 ml of methylene chloride. The extract is washed with water and subsequently discarded. The combined aqueous phases are adjusted to pH 10–11 with 3N aqueous sodium hydroxide solution and extracted six times with 150 ml of methylene chloride/isopropanol (4:1) each time. The combined extracts are dried over potassium carbonate and evaporated, whereby there are obtained 21.6 g of 1-[6-(methylamino)hexyl]-2-benzimidazolinone as an oil.

EXAMPLE 18

In analogy to Example 17, by reacting [1S,2S]-2-(6-fluoro-1,2,3,4-tetrahydro-2-hydroxy-1-isopropyl-2-naphthyl)ethyl p-toluenesulphonate and 1-methyl-3-[6-(methylamino)hexyl]-2-benzimidazolinone there is obtained 1-[6-[[2-[[7S,2S]-6-fluoro-1,2,3,4-tetrahydro-2-hydroxy-1-isopropyl-2-naphthyl]ethyl]methylamino]hexyl]-3-methyl-2-benzimidazolinone as an oil.

The 1-methyl-3-[6-(methylamino)hexyl]-2-benzimidazolinone used as the starting material was prepared as follows:

A solution of 9.7 g (44.5 mmol) of di-tert.-butyl dicarbonate in 50 ml of methanol is added dropwise at room temperature to 10.0 g (40.4 mmol) of 1-[6-(methylamino)hexyl]-2-benzimidazolinone in 150 ml of methanol and the reaction mixture is stirred at room temperature for 16 hours. Thereafter, 6.9 ml (49.5 mmol) of triethylamine and a further 9.7 g of di-tert.-butyl dicarbonate in 50 ml of methanol are added and the mixture is stirred at room temperature for a further 16 hours. Thereafter, the reaction mixture is poured into 200 ml of water and extracted with 400 ml of methylene chloride. The extracts are washed with water, dried over potassium carbonate and evaporated, whereby there are obtained 14.1 g of tert.-butyl methyl [6-(2-oxo-1-benzimidazolinyl)hexyl]carbamate as an oil.

2.6 g (59.6 mmol) of a 55% sodium hydride dispersion in mineral oil are washed oil-free with hexane and subsequently covered with 30 ml of dimethylformamide. To this suspension are added dropwise at room temperature within 20 minutes 13.8 g (39.7 mmol) of tert.-butyl methyl [6-(2-oxo-1-benzimidazolinyl)hexyl]carbamate in 90 ml of dimethylformamide. After stirring at room temperature for 90 minutes, 6.2 ml (99.3 mmol) of methyl iodide in 30 ml of dimethylformamide are added dropwise at room temperature and the reaction mixture is stirred at this temperature for a further 16 hours. For the work-up, the mixture is poured into 200 ml of water and extracted with 300 ml of methylene chloride. The methylene chloride extract is washed with water, dried over potassium carbonate and concentrated. The residue is chromatographed on 110 g of silica gel with methylene chloride and methylene chloride/isopropanol (99:1 and 98:2), whereby there are obtained 9.0 g of tert.-butyl methyl [6-(3-methyl-2-oxo-1-benzimidazolinyl)hexyl]carbamate as an oil.

In analogy to Example 17, last paragraph, from the compound obtained above there was obtained 1-methyl-3-[6-(methylamino)hexyl]-2-benzimidazolinone as an oil.

EXAMPLE 19

In an analoqous manner to that described in Example 17, by reacting [1S,2S]-2-(6-fluoro-1,2,3,4-tetrahydro-2-hydroxy-1-isopropyl-2-naphthyl)ethyl p-toluenesulphonate and 1-[p-[4-(methylamino)butyl]phenyl]imidazole there was obtained [1S,2S]-6-fluoro-1,2,3,4-tetrahydro-1-isopropyl- 2-[2-[[4-[p-(imidazol-1-yl)phenyl]butyl]methylamino]ethyl]-2-naphthalenol as an oil.

The 1-[p-[4-(methylamino)butyl]phenyl]imidazole used as the starting material was prepared as follows:

(a) 53.1 g (116 mmol) of [2-(m-dioxan-2-yl)ethyl]triphenylphosphonium bromide are suspended in 160 ml of tetrahydrofuran and treated at −25° within 15 minutes with 77.3 ml (116 mmol) of n-butyllithium solution (about 1.5M in hexane). Thereafter, the mixture is stirred at −25° for 15 minutes. Subsequently, 10 ml of a mixture of tetrahydrofuran and 1,3-dimethyl-3,4,5,6-tetrahydro-2-(1H)-pyrimidinone (1:1) are added, the mixture is stirred at −25° for a further 5 minutes and then treated within 30 minutes at −25° with 20 g (116 mmol) of p-(imidazol-1-yl)-benzaldehyde in 150 ml of tetrahydrofuran/1,3-dimethyl-3,4,5,6-tetrahydro-2-(1H)-pyrimidinone (1:1). After completion of the addition the reaction mixture is warmed to room temperature and stirred at this temperature for 15 minutes. Thereafter, the reaction mixture is poured into 1 l of ice-water and extracted with 600 ml of methylene chloride. The methylene chloride extract is washed with water, dried over magnesium sulphate and evaporated. There are thus obtained 42.2 g of a semi-crystalline product which is dissolved in 600 ml of methanol and hydrogenated exhaustively in the presence of 18 g of palladium-on-carbon (5%). After filtering off the catalyst and evaporation of the filtrate there are obtained 36.6 g of a semi-crystalline residue which, in turn, is dissolved in 700 ml of methanol, treated with 22.4 g of p-toluenesulphonic acid monohydrate and heated to reflux for 2.5 hours. After cooling to room temperature the pH value is adjusted to 7 with 36 g of sodium carbonate, the reaction mixture is evaporated, the residue is poured into 500 ml of water and extracted with 600 ml of methylene chloride. The methylene chloride extract is washed with water and saturated sodium chloride solution, dried over magnesium sulphate and evaporated, whereby there are obtained 36.1 g of a semi-crystalline residue. This is dissolved in 400 ml of tetrahydrofuran, treated with 110 ml of 3N aqueous hydrochloric acid, stirred at room temperature for 3 hours and subsequently concentrated under reduced pressure. Thereafter, the reaction mixture is poured into 500 ml of ice-water and extracted three times with 200 ml of ether each time. The aqueous phase is subsequently adjusted to pH 9 with potassium carbonate and extracted with 600 ml of methylene chloride. The methylene chloride extract is washed with water, dried over potassium carbonate and evaporated. The residue is chromatographed on 240 g of silica gel with methylene chloride and 0–5% isopropanol as the elution agent. There are thus obtained 13.2 g (53%) of 4-[p-(imidazol-1-yl)phenyl]butanal as an oil.

(b) 37.8 g (558 mmol) of methylamine hydrochloride are dissolved in 200 ml of methanol and thereupon treated with 45.8 g (558 mmol) of sodium acetate and 3.9 g (62.1 mmol) of sodium cyanoborohydride. The reaction mixture is stirred at room temperature for 15 minutes and thereafter 12.05 g (56.24 mmol) of 4-[p-(imidazol-1-yl)phenyl]butanal in 40 ml of methanol are added dropwise at room temperature within 15 minutes and the reaction mixture is stirred at room temperature for 3 hours. Thereafter, the reaction mixture is concentrated under reduced pressure, the residue is poured into 1 l of ice-water and extracted with 800 ml of methylene chloride. The organic extract is washed with water, dried over magnesium sulphate and evaporated. The residue obtained is chromatographed on 100 g of silica gel with methylene chloride/isopropanol/aqueous, 25% ammonia (160:40:1 and 7:3:0.3, respectively), whereby there are obtained 3.8 g (29%) of 1-[p-[4-(methylamino)butyl]phenyl]imidazole as an oil.

EXAMPLE 20

In an analogous manner to that described in Example 15, by reacting [1S,2S]-2-(6-fluoro-1,2,3,4-tetrahydro-2hydroxy-1-isopropyl-2-naphthyl)ethyl p-toluenesulphonate and 1-[4-(methylamino)butyl]-2-benzimidazolinone there was obtained 1-[4-[[2-[[1S,2S]-6-fluoro-1,2 3,4-tetrahydro-2-hydroxy-1-isopropyl-2-naphthyl]ethyl]methylamino]butyl]-2-benzimidazolinone as an oil.

The 1-[4-(methylamino)butyl]-2-benzimidazolinone used as the starting material was prepared as follows:

In analogy to Example 17, from 4-(methylamino)-1-butanol there was obtained tert.-butyl methyl [4-[(methylsulphonyl)oxy]butyl]carbamate as an oil which was then converted into tert.-butyl methyl [4-[3-(1-methylvinyl)-2-oxo-1-benzimidazolinyl]butyl]carbamate. This compound, likewise obtained as an oil, was then converted, again in analogy to Example 17, into 1-[4-(methylamino)butyl]-2-benzimidazolinone which was again obtained as an oil.

EXAMPLE 21

In an analogous manner to that described in Example 17, by reacting [1S,2S]-2-(6-fluoro-1,2,3,4-tetrahydro-2-hydroxy-1-isopropyl-2-naphthyl)ethyl p-toluenesulphonate and 1-isopropyl-3-[4-(methylamino)butyl]-2-benzimidazolinone there was obtiined 1-[4-[[2-[[1S,2S]-6-fluoro-1,2,3,4-tetrahydro-2-hydroxy-1-isopropyl-2-naphthyl]ethyl]methylamino]butyl]-3-isopropyl-2-benzimidazolinone as an oil.

The 1-isopropyl-3-[4-(methylamino)butyl]-2-benzimidazolinone used as the starting material was prepared as follows:

8.14 g (22.6 mmol) of tert.-butyl methyl [4-[3-(1-methylvinyl)-2-oxo-1-benzimidazolinyl]butyl]carbamate are dissolved in 80 ml of methanol and, after the addition of 1.6 g of palladium-on-carbon (5%), hydrogenated for 4 hours. Thereupon, the reaction mixture is filtered and evaporated, whereby there are obtained 8.5 g of tert.-butyl methyl [4-(3-isopropyl-2-oxo-1-benzimidazolinyl)butyl]carbamate as an oil. This is converted in analogy to the last paragraph of Example 17 into 1-isopropyl-3-[4-(methylamino)butyl]-2-benzimidazolinone which is likewise obtained as an oil.

EXAMPLE 22

In an analogous manner to that described in Example 17, by reacting [1S,2S]-2-(6-fluoro-1,2,3,4-tetrahydro-2-hydroxy-1-isopropyl-2-naphthyl)ethyl p-toluenesulphonate and 1-butyl-3-[6-(methylamino)hexyl]-2-benzimidazolinone there was obtained 1-[6-[[2-[[1S,2S]-6-fluoro-1,2,3,4-tetrahydro-2-hydroxy-1-isopropyl-2-naphthyl]ethyl]methylamino]hexyl]-3-butyl-2-benzimidazolinone as an oil.

The 1-butyl-3-[6-(methylamino)hexyl]-2-benzimidazolinone used as the starting material was prepared as follows:

In analogy to Example 18, from tert.-butyl methyl [6-(2-oxo-1-benzimidazolinyl)hexyl]carbamate and butyl iodide there was obtained tert.-butyl methyl [6-(3-butyl-2-oxo-1-benzimidazolinyl)hexyl]carbamate as an oil. This compound was converted in analogy to Example 17 into 1-butyl-3-[6-(methylamino)hexyl]-2-benzimidazolinone which was likewise obtained as an oil.

EXAMPLE 23

In an analogous manner to lhat described in Example 17, by reacting [1S,2S]-2-(6-fluoro-1,2,3,4-tetrahydro-2-hydroxy-1-isopropyl-2-naphthyl)ethyl p-toluenesulphonate and 1-(2-morpholinoethyl)-3-[6-(methylamino)hexyl]-2-benzimidazolinone there was obtained 1-[6-[[2-[[1S,2S]-6-fluoro-1,2,3,4-tetrahydro-2-hydroxy-1-isopropyl-2-naphthyl]ethyl]methylamino]hexyl]-3-(2-morpholinoethyl)-2-benzimidazolinone as an oil.

The 1-(2-morpholinoethyl)-3-[6-(methylamino)hexyl]-2-benzimidazolinone used as the starting material was prepared as follows:

9.0 g (25.9 mmol) of tert.-butyl methyl [6-(2-oxo-1-benzimidazolinyl)hexyl]carbamate are dissolved in 250 ml of methanol and treated with 35 g (259 mmol) of potassium carbamate, 0.5 g of potassium iodide and portionwise with 16.9 g (90.6 mmol) of chloroethylmorpholine hydrochloride. Thereafter, the reaction mixture is heated to reflux for 16 hours. After cooling the reaction mixture is poured into 1 l of ice-water and extracted with 800 ml of methylene chloride. The extract is washed with water, dried and concentrated. The residue is dissolved in 50 ml of ether and extracted in each case once with 15 ml and 5 ml of 3N methanesulphonic acid in water and once with 5 ml of water. The combined aqueous phases are adjusted to pH 8-9 With ammonia and extracted three times with 100 ml of methylene chloride each time. The combined extracts are washed with water, dried over potassium carbonate and evaporated, whereby there are obtained 7.8 g (65.4%) of tert.-butyl methyl [6-[3-(2-morpholinoethyl)-2-oxo-1-benzimidazolinyl]hexyl]carbamate as an oil.

This was then converted, likewise in analogy to Example 17, into 1-(2-morpholinoethyl)-3-[6-(methylamino)hexyl]-2-benzimidazolinone dihydrochloride, m.p. 229°-232°.

EXAMPLE 24

In an analogous manner to that described in Example 17, by reacting [1S,2S]-2-(6-fluoro-1,2,3,4-tetrahydro-2-hydroxy-1-isopropyl-2-naphthyl)ethyl p-toluenesulphonate and 1-benzyl-3-[4-(methylamino)butyl]-2-benzimidazolinone there was obtained 1-benzyl-3-[4-[[2-[[1S,2S]-6-fluoro-1.2,3,4-tetrahydro-2-hydroxy-1-isopropyl-2-naphthyl]ethyl]methylamino]butyl]-2-benzimidazolinone as an oil.

The 1-benzyl-3-[4-(methylamino)butyl]-2-benzimidazolinone used as the starting material was prepared in analogy to Example 18 from 1-[4-(methylamino)butyl]-2-benzimidazolinone via tert.-butyl methyl [4-(2-oxo-1-benzimidazolinyl)butyl]carbamate.

EXAMPLE 25

In an analogous manner to that described in Example 17, by reacting [1S,2S]-2-(6-fluoro-1,2,3,4-tetrahydro-2-hydroxy-1-isopropyl-2-naphthyl)ethyl p-toluenesulphonate and 1-[4-(methylamino)butyl]-3-(2-pyridylmethyl)-2-benzimidazolinone there was obtained 1-[4-[[2-[[1S,2S]-6-fluoro-1,2,3,4-tetrahydro-2-hydroxy-1-isopropyl-2-naphthyl]ethyl]methylamino]butyl]-3-(2-pyridylmethyl)-2-benzimidazolinone as an oil.

The 1-[4-(methylamino)butyl]-3-(2-pyridylmethyl)-2-benzimidazolinone used as the starting material was prepared in analogy to Example 18 from tert.-butyl methyl [4-(2-oxo-1-benzimidazolinyl)butyl]carbamate.

EXAMPLE 26

In an analogous manner to that described in Example 15, by reacting [1S,2S]-2-(6-fluoro-1,2,3,4-tetrahydro-2-hydroxy-1-isopropyl-2-naphthyl)ethyl p-toluenesulphonate and 1,3-dihydro-3-[6-(methylamino)hexyl]-2H-imidazo[4,5-c]pyridin-2-one there was obtained 3-[6-[[2-[[1S,2S]-6-fluoro-1,2,3,4-tetrahydro-2-hydroxy-1-isopropyl-2-naphthyl]ethyl]methylamino]hexyl]-1,3-dihydro-2H-imidazo[4.5-c]pyridin-2-one as an oil.

The 1,3-dihydro-3-[6-(methylamino)hexyl]-2H-imidazo[4.5-c]pyridin-2-one used as the starting material was prepared as follows:

In an analogous manner to that described in Example 17, from 6-(methylamino)-1-hexanol there was obtained tert.-butyl methyl (6-hydroxyhexyl)carbamate as an oil which was then converted via tert.-butyl methyl [6-[(methylsulphonyl)oxy]hexyl]carbamate, likewise obtained as an oil, into tert.-butyl methyl [6-[1-(1-methylvinyl)-1,2-dihydro-2-oxo-3H-imidazo[4,5-c]pyridin-3-yl]hexyl]carbamate; the product was again obtained as an oil.

12.2 g (31.4 mmol) of the last-named compound are dissolved in 100 ml of ethanol, treated with 13 ml of concentrated aqueous hydrochloric acid and heated to reflux for 40 hours. Thereafter, the mixture is adjusted to pH 9–10 with dilute aqueous sodium hydroxide solution while cooling with ice, the reaction solution is saturated with sodium chloride and extracted continuously with chloroform for 16 hours. The extract is dried over potassium carbonate and evaporated, whereby there are obtained 7.2 g (92%) of 1,3-dihydro-3-[6-(methylamino)hexyl]-2H-imidazo[4,5-c]pyridin-2-one as an oil which is processed without further purification.

EXAMPLE 27

The following compounds were prepared in an analogous manner to that described in Example 16:

[1S,2S]-6-fluoro-1,2,3,4-tetrahydro-1-isopropyl-2-[2-[methyl-[6-(2-oxo-1-benzimidazolinyl)hexyl]amino]ethyl]-2-naphthyl methoxyacetate hydrochloride, $[\alpha]_D^{20} = +27.8°$ (c=1%; methanol);

[1S,2S]-6-fluoro-1,2,3,4-tetrahydro-1-isopropyl-2-[2-[methyl-[4-(2-oxo-1-benzimidazolinyl)butyl]amino]ethyl]-2-naphthyl methoxyacetate hydrochloride, $[\alpha]_D^{20} = +28.7°$ (c=1%; methanol);

[1S,2S]-2-[2-[[6-(1,2-dihydro-2-oxo-3H-imidazo[4,5-c]pyridin-3-yl)hexyl]methylamino]ethyl]-6-fluoro-1,2,3,4-tetrahydro-1-isopropyl-2-naphthyl methoxyacetate dihydrochloride, $[\alpha]_D^{20} = +26.0°$ (c=1%; methanol).

EXAMPLE 28

4.6 g (9.3 mmol) of 1-[6-[[2-[[1S,2S]-6-fluoro-1,2,3,4-tetrahydro-2-hydroxy-1-isopropyl-2-naphthyl]ethyl]methylamino]hexyl]-3-methyl-2-benzimidazolinone are dissolved in 15 ml of methylene chloride, treated with 1.9 ml of pyridine and 6.2 g (38 mmol) of methoxyacetic anhydride and stirred at room temperature for 20 hours. Thereafter, the mixture is treated with 45 ml of 1N aqueous sodium hydroxide solution while cooling with ice and stirred at 10°–15° for 1 hour. The reaction mixture is subsequently poured into 400 ml of ice-water and extracted with 600 ml of methylene chloride. The extract is washed with water, dried over potassium carbonate, evaporated, treated with one equivalent of hydrochloric acid in ethanol and evaporated. There are thus obtained 5.3 g of [1S,2S]-6-fluoro-1,2,3,4-tetrahydro-1-isopropyl-2-[2-[methyl-[6-(3-methyl-2-oxo-1-benzimidazolinyl)hexyl]amino]ethyl]-2-naphthyl methoxyacetate hydrochloride, $[\alpha]_D^{20} = +27.1°$ (c=1%; methanol).

EXAMPLE 29

The following compounds were manufactured in analogy to Example 28:

[1S,2S]-6-fluoro-1,2,3,4-tetrahydro-1-isopropyl-2-[2-[[4-[p-(imidazol-1-yl)phenyl]butyl]methylamino]ethyl]-2-naphthyl methoxyacetate oxalate (1:1), $[\alpha]_D^{20} = +27.6°$ (c=1%; methanol);

[1S,2S]-6-fluoro-1,2,3,4-tetrahydro-1-isopropyl-2-[2-[methyl-[4-(3-isopropyl-2-oxo-1-benzimidazolinyl)butyl]amino]ethyl]-2-naphthyl methoxyacetate hydrochloride, $[\alpha]_D^{20} = +27.6°$ (c=1%; methanol);

[1S,2S]-6-fluoro-1,2,3,4-tetrahydro-1-isopropyl-2-[2-[methyl-[6-(3-butyl-2-oxo-1-benzimidazolinyl)hexyl]amino]ethyl]-2-naphthyl methoxyacetate hydrochloride, $[\alpha]_D^{20} = +26.4°$ (c=1%; methanol);

[1S,2S]-6-fluoro-1,2,3,4-tetrahydro-1-isopropyl-2-[2-[methyl-[6-[3-(2-morpholinoethyl)-2-oxo-1-benzimidazolinyl]hexyl]amino]ethyl]-2-naphthyl methoxyacetate dihydrochloride, $[\alpha]_D^{20} = +22.4°$ (c=1%; methanol);

[1S,2S]-2-[2-[[4-(3-benzyl-2-oxo-1-benzimidazolinyl)butyl]methylamino]ethyl]-6-fluoro-1,2,3,4-tetrahydro-1-isopropyl-2-naphthyl methoxyacetate hydrochloride, $[\alpha]_D^{20} = +25.6°$ (c=1%; methanol);

[1S,2S]-6-fluoro-1,2,3,4-tetrahydro-1-isopropyl-2-[2-[methyl-[4-[2-oxo-3-(2-pyridylmethyl)-1-benzimidazolinyl]butyl]amino]ethyl]-2-naphthyl methoxyacetate dihydrochloride, $[\alpha]_D^{20} = +23.3°$ (c=1%; methanol).

EXAMPLE 30

1.3 g (3.1 mmol) of [1S,2S]-2-[2-[[3-(2-benzimidazolyl)propyl]methylamino]ethyl]-6-fluoro-1,2,3,4-tetrahydro-1-isopropyl-2-naphthalenol in 10 ml of dimethylformamide are treated at room temperature with 0.19 g (1,53 mmol) of 4-dimethylaminopyridine, 1.7 ml (12.3 mmol) of triethylamine and a solution of 0.96 ml (9.24 mmol) of isobutyryl chloride in 5 ml of dimethylformamide and stirred at room temperature for 2 hours. Thereafter, the reaction mixture is poured into 20 ml of ice-water, treated with 10 ml of 1N aqueous sodium hydroxide solution, stirred at 0° for 10 minutes and extracted with 100 ml of methylene chloride. The extract is washed with water. dried over potassium carbonate and evaporated. The thus-obtained product is dissolved in 20 ml of methanol, treated with 1.5 ml of 1N aqueous sodium hydroxide solution, stirred at room temperature for 1 hour, poured into 50 ml of water and extracted with 100 ml of methylene chloride. The extract is washed with water, dried over magnesium sulphate and evaporated. The residue is chromatographed on 30 g of silica gel with methylene chloride and 1–20% isopropanol and on 20 g of silica gel with methylene chloride/isopropanol/25% aqueous ammonia (9:1:0.1). There are thus obtained 360 mg (21%) of [1S,2S]-2-[2-[[3-(2-benzimidazolyl)propyl]methylamino]ethyl]-6-fluoro-1,2,3,4-tetrahydro-1-isopropyl-2-naphthyl isobutyrate dihydrochloride.

EXAMPLE 31

A solution of 2.32 g (0.005 mol) of [1S,2S]-6-fluoro-1,2,3,4-tetrahydro-1-isopropyl-2-[2-[methyl-[5-(1-methyl-2-benzimidazolyl)pentyl]amino]ethyl]-2-naphthalenol and 0.6 g (0 005 mol) of phenyl isocyanate in 5 ml of toluene is treated with 7.5 mg of tin(II) 2-ethylhexanoate and heated to 100° for 15 hours. After concentration under reduced pressure the oily residue is chromatographed on 160 g of silica gel with methanol/methylene chloride (3:2) as the elution agent. The oily product obtained is dissolved in methylene chloride and treated with an excess of hydrogen chloride in ether. There are obtained 2.15 g (65%) of [1S,2S]-6-fluoro-1,2,3,4-tetrahydro-1-isopropyl-2-[2-[methyl-[5-(1-methyl-2-benzimidazolyl)pentyl]amino]ethyl]-2-naphthyl carbanilate dihydrochloride, m.p. 157°–160°, as a colourless crystalline powder.

EXAMPLE 32

The following compounds were obtained in an analogous manner to that described in Example 31:

[1S,2S]-6-fluoro-1,2,3,4-tetrahydro-1-isopropyl-2-[2-[methyl-[5-(1-methyl-2-benzimidazolyl)pentyl]amino]ethyl]-2-naphthyl butylcarbamate dihydrochloride, m.p. 156°–158°;

[1S,2S]-6-fluoro-1,2,3,4-tetrahydro-1-isopropyl-2-[2-[methyl-[5-(1-methyl-2-benzimidazolyl)pentyl]amino]ethyl]-2-naphthyl benzylcarbamate dihydrochloride, m.p. 132°–136°;

[1S,2S]-6-fluoro-1,2,3,4-tetrahydro-1-isopropyl-2-[2-[methyl[5-(1-methyl-2-benzimidazolyl)pentyl]amino]ethyl]-2-naphthyl p-chlorocarbanilate dihydrochloride, m.p. 159°–163°.

EXAMPLE 33

A mixture of 4.67 g (11.5 mmol) of [1S,2S]-2-(6-fluoro-1,2,3,4-tetrahydro-2-hydroxy-1-isopropyl-2-naphthyl)ethyl p-toluenesulphonate, 3.5 g (11.5 mmol) of 1-methyl-2-[3-(methylamino)propyl]-4,5-diphenylimidazole and 1.5 g (11.5 mmol) of N-ethyldiisopropylamine is stirred at 100° for 1 hour. The cooled mass is partitioned between water and methylene chloride and the organic phase is washed with a saturated solution of sodium chloride. dried over sodium sulphate and concentrated to dryness. The residual oil is chromatographed on 400 g of silica gel with methylene chloride/methanol (4:1) as the elution agent. The purified condensation product (5.3 of oil) is dissolved in 15 ml of methoxyacetic anhydride, treated with 0.85 ml of pyridine and the solution is stirred at 70° for 2 hours. The cooled reaction mixture is partitioned between 400 ml of methylene chloride and 400 ml of 3N aqueous sodium hydroxide solution and the mixture is stirred intensively at room temperature for 15 minutes. The separated aqueous phase is again extracted with 400 ml of methylene chloride, the combined extracts are washed with a saturated aqueous solution of sodium chloride, dried over sodium sulphate and concentrated to dryness. The oily residue is chromatographed on 350 g of silica gel with methylene chloride/methanol (9:1) as the elution agent. The oil obtained from the homogeneous fractions is dissolved in ethyl acetate and treated with an excess of hydrogen chloride in ether. The crystallizate is filtered off, washed with ether and dried. There are obtained 4.0 g (51%) of [1S,2S]-6-fluoro-1,2,3,4-tetrahydro-1-isopropyl-2-[2-[[3-(1-methyl-4,5-diphenylimidazol-2-yl)propyl]methylamino]ethyl]-2-naphthyl methoxyacetate dihydrochloride, m.p. 185°–189°, as an almost colourless crystalline powder.

The 1-methyl-2-[3-(methylamino)propyl]-4,5-diphenylimidazole used as the starting material was prepared as follows:

3.2 ml (0.024 mol) of isobutyl chloroformate are added dropwise at −5° to a solution of 7.0 g (0.024 mol) of 4,5-diphenylimidazole-2-propionic acid and 3.36 ml (0.024 mol) of triethylamine in 80 ml of dimethylformamide. After stirring at 0°–5° for 30 minutes 1.64 g (0.024 mol) of methylamine hydrochloride and 3.36 ml (0.024 mol) of triethylamine in 32 ml of dimethylformamide and 1.65 ml of water are added. The temperature is then left to rise to room temperature and the mixture is stirred for a further 20 hours. After concentration under reduced pressure the residue is boiled up in 250 ml of methanol and treated with 3.6 ml (0.024 mol) of 1,8-diazabicyclo[5.4.0]undec-7-ene (DBU), whereby a clear solution results. 4.8 g of N-methyl-4,5-diphenylimidazole-2-propionamide, m.p. 195°–200° (dec.), result by cooling in an ice-bath. From the mother liquor there are obtained by concentration and treatment with water a further 2 g of the same product, m.p. 195°–200°. Total yield: 6.8 g (93%).

9.15 g (0.03 mol) of N-methyl-4,5-diphenylimidazole-2-propionamide are added portionwise to a stirred suspension of 2.3 g (0.06 mol) of lithium aluminium hydride in 160 ml of tetrahydrofuran and the mixture is subsequently heated to reflux for 4 hours. At 5°–10° there are added dropwise thereto 6 ml of water, then 9 ml of a 10% solution of potassium hydroxide and again 6 ml of water. The precipitate is filtered off and boiled up three times with 50 ml of tetrahydrofuran each time. The combined filtrates are washed with a saturated aqueous solution of sodium chloride, dried over sodium sulphate and concentrated to dryness under reduced pressure. The oily residue is chromatographed on 200 g of silica gel firstly with chloroform/ethanol (9:1) and then with methanol as the elution agent. The first fractions which are eluted homogeneous give, after evaporation and trituration with ether, 1.2 g of starting material. The following fractions which are eluted homogeneous yield, after the same treatment, 5.5 g (73%) of 2-[3-(methylamino)propyl]-4,5-diphenylimidazole in the form of colourless crystals, m.p. 110°–113°.

A solution of 5.25 g (0.018 mol) of 2-[3-(methylamino)propyl]-4,5-diphenylimidazole and 3.8 ml (0.028 mol) of benzyl chloroformate in 38 ml of dimethylformamide is treated with 5 g of finely ground dry potassium carbonate and thereupon stirred intensively at room temperature for 1 hour. The inorganic salts are then filtered off, washed with methylene chloride and the filtrate is concentrated to dryness under reduced pressure. The oily residue is chromatographed on 500 g of silica gel with ethyl acetate as the elution agent. The homogeneous fractions give, after evaporation and trituration of the residue with hexane, 6.5 g (85%) of 2-[3-(N-benzyloxycarbonylmethylamino)propyl]-4,5-diphenylimidazole in the form of colourless crystals, m.p. 105°–108°.

A solution of 6.4 g (0.015 mol) of 2-[3-(N-benzyloxycarbonylmethylamino)propyl]-4,5-diphenylimidazole in 120 ml of dimethylformamide is treated at 15°–20° under argon with 0.018 mol of sodium hydride (0.8 g of a 55% dispersion in mineral oil) and thereupon stirred at room temperature for a further 30 minutes. A solution of 1.85 ml (0.03 mol) of methyl iodide in 10 ml of dimethylformamide is added thereto at 15°–20° within 15 minutes and the mixture is stirred at room temperature for a further 3 hours. After concentration under reduced pressure the residue is partitioned between ice-water and ethyl acetate. The organic phase, dried over sodium sulphate, is evaporated and the residual oil is chromatographed on 100 g of silica gel with ethyl acetate as the elution agent. The 2-[3-(N-benzyloxycarbonylmethylamino)propyl]-1-methyl-4,5-diphenylimidazole (6.4 g of oil) obtained is dissolved in 300 ml of methanol and hydrogenated at room temperature and normal pressure in the presence of 1 g of 5% palladium-on-active charcoal. The product, isolated in the usual manner, is chromatographed on 70 g of silica gel with methanol/concentrated ammonium hydroxide (100:1) as the elution agent. There are obtained 2.95 g (64%) of 1-methyl-2-[3-(methylamino)propyl]-4,5-diphenylimidazole as a thick oil.

EXAMPLE 34

In an analoqous manner to that described in Example 33, [1S,2S]-2-(6-fluoro-1,2,3,4-tetrahydro-2-hydroxy-1-isopropyl-2-naphthyl)ethyl p-toluenesulphonate is reacted firstly with 2-[3-(methylamino)propyl]-4,5-diphenylimidazole and then with methoxyacetic anhydride. There is obtained [1S,2S]-6-fluoro-1,2,3,4-tetrahydro-1-isopropyl-2-[2-[[3-(4,5-diphenylimidazol-2-yl)propyl]methylamino]ethyl]-2-naphthyl methoxyacetate dihydrochloride, m p. 160°–164°, as a colourless crystalline powder.

EXAMPLE 35

In an analogous manner to that described in Example 33, [1S,2S]-2-(6-fluoro-1,2,3,4-tetrahydro-2-hydroxy-1-isopropyl-2-naphthyl)ethyl p-toluenesulphonate is reacted firstly with 2-[4-[(methylamino)methyl]benzyl]-1-methyl-benzimidazole and then with methoxyacetic anhydride. There is obtained [1S,2S]-6-fluoro-1,2,3,4-tetrahydro-1-isopropyl-2-[2-[[4-[(1-methyl-2-benzimidazolyl)methyl]benzyl]methylamino]ethyl]-2-naphthyl methoxyacetate dihydrochloride, m.p. 130°–134°, as an almost colourless crystalline powder.

The 2-[4-[(methylamino)methyl]benzyl]-1-methyl-benzimidazole used as the starting material was prepared as follows:

A mixture of 30 g (0.277 mol) of o-phenylenediamine and 150 g of polyphosphoric acid ester (ppE) is heated to 120°. When the diamine has dissolved, 33 g (0.205 mol) of p-cyanophenylacetic acid are added thereto in one portion and the mixture is heated to 120° for a further 20 minutes. After cooling to room temperature the viscous mass is treated with about 1 l of water and made weakly basic with solid sodium hydrogen carbonate. The mixture is extracted with methylene chloride and the extract is washed with water, dried over sodium sulphate and evaporated to dryness. Recrystallization of the residue from methylene chloride/ethyl acetate gives 29 g (60%) of 2-(p-cyanobenzyl)benzimidazole, m.p. 201°–203°, as a colourless crystalline powder.

A solution of 21.9 g of 2-(p-cyanobenzyl)benzimidazole in a mixture of 140 ml of methanol and 140 ml of liquid ammonia is hydrogenated at room temperature and 30 bar in the presence of 5 g of Raney-nickel. The product, isolated in the usual manner, is chromatographed on 400 g of silica gel with methanol as the elution agent. The homogeneous fractions give, after evaporation and trituration of the residue with ether, 14.7 g (66%) of 2-[p-(aminomethyl)benzyl]benzimidazole, m.p. 133°–136°, as a pale brown crystalline powder.

A solution of 9.2 g (0.04 mol) of 2-[p-(aminomethyl)benzyl]benzimidazole and 8.4 ml (0.06 mol) of benzyl chloroformate in 80 ml of dimethylformamide is treated with 10 g of finely ground dry potassium carbonate and thereupon stirred intensively at room temperature for 30 minutes. 12 ml (0.08 mol) of 1,8-diazabicyclo[5.4.0]undec-7-ene (DBU) are then added thereto and the mixture is stirred at room temperature for a further 30 minutes. The inorganic salts are filtered off, rinsed with methylene chloride and the filtrate is concentrated to dryness under reduced pressure. The oily residue is chromatographed on 600 g of silica gel firstly with methylene chloride/ethyl acetate (4:1) and then with chloroform/ethanol (9:1) as the elution agent. The fractions eluted with chloroform/ethanol give, after evaporation and trituration with ethyl acetate, 10.8 g (73%) of benzyl [4-[2-(benzimidazolyl)methyl]benzyl]carbamate, m.p. 190°–194°, as a colourless crystalline powder.

A solution of 8.9 g (0.024 mol) of benzyl [4-[2-(benzimidazolyl)methyl]benzyl]carbamate in 210 ml of dimethylformamide is treated at 15°–20° under argon with 0.056 mol of sodium hydride (2.5 g of a 55% dispersion in mineral oil) and thereupon stirred at room temperature for a further 30 minutes. A solution of 7.4 ml (0.12 mol) of methyl iodide in 22 ml of dimethylformamide is added thereto at 15°–20° within 20 minutes and the mixture is stirred at room temperature for a further 10 minutes. After concentration under reduced pressure the residue is partitioned between ice-water and ethyl acetate. The organic phase, dried over sodium sulphate, is evaporated and the residual oil is chromatographed on 300 g of silica gel with methylene chloride/ethyl acetate (1:1) as the elution agent. The first fractions which are eluted homogeneous yield, after evaporation and trituration with ether, 4.5 g (45%) of benzyl [4-[1-(1-methyl-2-benzimidazolyl)ethyl]benzyl]methylcarbamate, m.p. 131°–133°, as a colourless crystalline powder. The following fractions which are eluted homogeneous give, after concentration, 3.5 g (37%) of benzyl [4-[(1-methyl-2-benzimidazolyl)methyl]benzyl]methylcarbamate as a viscous oil.

3.5 g of benzyl [4-[(1-methyl-2-benzimidazolyl)methyl]benzyl]methylcarbamate are dissolved in 600 ml of methanol and hydrogenated at room temperature and normal pressure after the addition of 1 g of 5% palladium-on-active charcoal. The product, isolated in the usual manner, is chromatographed on 150 g of silica gel with methanol/concentrated ammonium hydroxide (100:1) as the elution agent. There are obtained 2.1 g (90%) of 2-[4-[(methylamino)methyl]benzyl]-1-methyl-benzimidazole as a thick oil.

EXAMPLE 36

In an analogous manner to that described in Example 33, [1S,2S]-2-(6-fluoro-1,2,3,4-tetrahydro-2-hydroxy-1-isopropyl-2-naphthyl)ethyl p-toluenesulphonate is reacted firstly with 2-[1-[4-[(methylamino)methyl]phenyl]ethyl]-1-methyl-benzimidazole and then with methoxyacetic anhydride. There is obtained [1S,2S]-6-fluoro-1,2,3,4-tetrahydro-1-isopropyl-2-[2-[[4-[1-(1-methyl-2-benzimidazolyl)ethyl]benzyl]methylamino]ethyl]-2-naphthyl methoxyacetate dihydrochloride (mixture of 2 epimers), m.p. 95°–105°, as an almost colourless crystalline powder.

The 2-[1-[4-[(methylamino)methyl]phenyl]ethyl]-1-methylbenzimidazole used as the starting material was prepared in an analogous manner to that given in Example 35 by hydrogenating benzyl [4-[1-(1-methyl-2-benzimidazolyl)ethyl]benzyl]methylcarbamate.

EXAMPLE 37

In an analogous manner to that described in Example 33, [1S,2S]-2-(6-fluoro-1,2,3,4-tetrahydro-2-hydroxy-1-isopropyl-2-naphthyl)ethyl p-toluenesulphonate is reacted firstly with 2-[4-[(methylamino)methyl]benzyl]-benzimidazole and then with methoxyacetic anhydride. There is obtained [1S,2S]-6-fluoro-1,2,3,4-tetrahydro-1-isopropyl-2-[2-[[4-[(2-benzimidazolyl)methyl]benzyl]methylamino]ethyl]-2-naphthyl methoxyacetate dihydrochloride, m.p. 146°–150°, as an almost colourless crystalline powder.

The 2-[4-[(methylamino)methyl]benzyl]benzimidazole used as the starting material was prepared as follows:

6.6 g (0.028 mol) of 2-(p-cyanobenzyl)benzimidazole are heated to reflux for 2 hours in 110 ml of 1N sodium hydroxide solution. The solution obtained is cooled and extracted twice with 100 ml of ethyl acetate and twice with 100 ml of methylene chloride. The aqueous phase is adjusted to pH 6.0 with 2N hydrochloric acid and left to stand in an ice-bath for 30 minutes. The precipitate is filtered off under suction and washed with ether. There are obtained 5.8 g (83%) of p-[(2-benzimidazolyl)methyl]benzoic acid, m.p. 265°–267°, as a colourless powder.

2.8 ml of butyl chloroformate are added dropwise at −5° to a solution of 5.0 g (0.020 mol) of p-[(2-benzimidazolyl)methyl]benzoic acid and 2.8 ml (0.020 mol) of triethylamine in 68 ml of dimethylformamide. After stirring at 0°–5° for 30 minutes 1.32 g (0.020 mol) of methylamine hydrochloride and 2.8 ml (0.020 mol) of triethylamine in 28 ml of dimethylformamide and 1.4 ml of water are added. The temperature is then left to rise to room temperature and the mixture is stirred for a further 18 hours. After concentration under reduced pressure the residue is chromatographed on 400 g of silica gel with chloroform/ethanol (4:1) as the elution agent. The uniform fractions give 2.0 g (38%) of N-methyl-p-[(2-benzimidazolyl)methyl]benzamide, m.p. 250°–255° (dec.), as a colourless powder.

1.98 g (0.0075 mol) of N-methyl-p-[(2-benzimidazolyl)methyl]benzamide are added portionwise to a stirred suspension of 0.58 g (0.0075 mol) of lithium aluminium hydride in 40 ml of tetrahydrofuran and subsequently heated to reflux for 4 hours. At 5°–10° there are added dropwise 1.5 ml of water, then 2.3 ml of a 10% solution of potassium hydroxide and again 1.5 ml of water. The precipitate is filtered off and boiled three times with 20 ml of tetrahydrofuran each time. The combined filtrates are washed with a saturated aqueous solution of sodium chloride, dried over sodium sulphate and concentrated to dryness under reduced pressure. The residue is chromatographed on 150 g of silica gel with methanol/concentrated ammonium hydroxide (100:1) as the elution agent. There are obtained 1.58 g (84%) of 2-[4-[(methylamino)methyl]benzyl]benzimidazole, m.p. 157°–160°, as a colourless crystalline powder.

EXAMPLE 38

In an analoqous manner to that described in Example 33, [1S,2S]-2-(6-fluoro-1,2,3,4-tetrahydro-2-hydroxy-1-lisopropyl-2-naphthyl)ethyl p-toluenesulphonate is reacted firstly with 2-[trans-4-[(methylamino)methyl]cyclohexyl]benzimidazole and then with methoxyacetic anhydride. There is obtained [1S,2S]-6-fluoro-1,2,3,4-tetrahydro-1-isopropyl-2-[2-[methyl-[trans-4-(2-benzimidazolyl)cyclohexyl]methylamino]ethyl]-2-naphthyl methoxyacetate dihydrochloride, m.p. 150°–153°, as a colourless crystalline powder.

The 2-[trans-4-[(methylamino)methyl]cyclohexyl]-benzimidazole used as the starting material was prepared as follows:

A solutionoof 20.3 g (0.07 mol) of trans-4-(N-benzyloxycarbonyl-aminomethyl)cyclohexanecarboxylic acid in 380 ml of dimethylformamide is treated at 15°–20° under argon with 0.21 mol of sodium hydride (9.35 g of a 55% dispersion in mineral oil) and thereupon stirred at room temperature for a further 30 minutes. A solution of 17.5 ml (0.28 mol) of methyl iodide in 20 ml of dimethylformamide is added thereto at 25°–30° within 20 minutes and the mixture is stirred at 70° for a further 1 hour. After concentration under reduced pressure the residue is partitioned between water and methylene chloride. The organic phase is evaporated and the residual oil is dissolved in a mixture of 350 ml of ethanol and 350 ml of 1N sodium hydroxide solution. The mixture is heated to reflux for 1 hour, cooled and poured into 700 ml of ice-water The solution is extracted with ethyl acetate and then acidified with 6N hydrochloric acid. The liberated acid is extracted with methylene chloride and the extract is dried over sodium sulphate and evaporated. The residual oil is chromatographed on 270 g of silica gel with a mixture of methylene chloride/ethyl acetate (4:1) as the elution agent. There are obtained 13.6 g (64%) of trans-4-(N-benzyloxycarbonyl-N-methyl-aminomethyl)cyclohexanecarboxylic acid as a thick oil.

A solution of 13.6 g (0.044 mol) of trans-4-(N-benzyloxycarbonyl-N-methyl-aminomethyl)cyclohexanecarboxylic acid and 9.5 ml (0.068 mol) of triethylamine in 110 ml of tetrahydrofuran is treated at −15° within 30 minutes with 6.5 ml (0.049 mol) of isobutyl chloroformate. A solution of 5.8 g (0.053 mol) of o-phenylenediamine is then added dropwise at −15° within 45 minutes. The mixture is stirred at room temperature for 1 hour and left to stand for 20 hours. After concentration under reduced pressure the residue is partitioned between water and ethyl acetate and the organic phase is washed with a 5% solution of sodium hydrogen carbonate, then with a saturated aqueous solution of sodium chloride and finally with water. The solution, dried over magnesium sulphate, is evaporated and triturated with ether. The solid product obtained (9.3 g) is dissolved in 200 ml of toluene, 3 g of p-toluenesulphonic acid are added thereto and the mixture is heated to reflux for 4 hours with a water separator. The solution is cooled, washed with a 2N sodium carbonate solution and a saturated aqueous solution of sodium chloride, dried over magnesium sulphate and concentrated to dryness under reduced pressure. The solid residue is recrystallized from ethyl acetate. There are obtained 5.6 g of benzyl [[trans-4-(2-benzimidazolyl)cyclohexyl]methyl]methylcarbamate, m.p. 146°–148°, as a colourless crystalline powder. After chromatography on 250 g of silica gel with ethyl acetate/methylene chloride (9:1) as the elution agent the mother liquor gives a further 1.1 g of the same product, m.p. 146°–148°. Total yield: 6.7 g (40%).

6.0 g of benzyl [[trans-4-(2-benzimidazolyl)cyclohexyl]methyl]methylcarbamate are dissolved in 600 ml of ethanol and hydrogenated at room temperature and normal pressure after the addition of 1 g of 5% palladium-on-active charcoal. The product, isolated in the usual manner, is recrystallized from methylene chloride/ether. There are obtained 3.0 g (78%) of 2-[trans-4-[(methylamino)methyl]cyclohexyl]benzimidazole, m.p. 232°–235°, as a colourless crystalline powder.

EXAMPLE 39

In an analogous manner to that described in Example 33, [1S,2S]-2-(6-fluoro-1,2,3,4-tetrahydro-2-hydroxy-1-isopropyl-2-naphthyl)ethyl p-toluenesulphonate is reacted firstly with 2-[trans-4-[(methylamino)methyl]cyclohexyl]-1-methyl-benzimidazole and then with methoxyacetic anhydride. There is obtained [1S,2S]-6-fluoro-1,2,3,4-tetrahydro-1-isopropyl-2-[2-[methyl-[trans-4-(1-methyl-2-benzimidazolyl)cyclohexyl]methylamino]ethyl]-2-naphthyl methoxyacetate dihydrochloride, m.p. 148°–152°, as a colourless crystalline powder.

The 2-[trans-4-[(methylamino)methyl]cyclohexyl]-1-methyl-benzimidazole used as the starting material was prepared as follows:

A solution of 7.2 g (0.019 mol) of benzyl [[trans-4-(2-benzimidazolyl)cyclohexyl]methyl]methylcarbamate in 160 ml of dimethylformamide is treated at 15°–20° under argon with 0.023 mol of sodium hydride (1.0 g of a 55% dispersion in mineral oil) and thereupon stirred at room temperature for a further 30 minutes. A solution of 2.3 ml (0.038 mol) of methyl iodide in 10 ml of dimethylformamide is added thereto at 15°–20° within 15 minutes and the mixture is stirred at room temperature for a further 3 hours. After concentration under reduced pressure the residue is partitioned between ice-water and ethyl acetate. The organic phase, dried over sodium sulphate, is evaporated and the solid residue is recrystallized from ethyl acetate/ether. There are obtained 5.9 g (79%) of benzyl [[trans-4-(1-methyl-2-benzimidazolyl)cyclohexyl]methyl]methylcarbamate, m.p. 141°–142°, as a colourless crystalline powder.

5.9 g of benzyl [[trans-4-(1-methyl-2-benzimidazolyl)cyclohexyl]methyl]methylcarbamate are dissolved in 600 ml of ethanol and hydrogenated at room temperature and normal pressure after the addition of 1 g of 5% palladium-on-active charcoal. The product. isolated in the usual manner, is chromatographed on 250 g of silica gel firstly with methylene chloride/methanol (1:1) and then with methanol/concentrated ammonium hydroxide (100:1) as the elution agent. There are obtained 3.3 g (85%) of 2-[trans-4-[(methylamino)methyl]cyclohexyl]-1-methyl-benzimidazole as a thick oil.

EXAMPLE 40

In an analogous manner to that described in Example 7, by reacting 2-(6-fluoro-1,2,3,4-tetrahydro-2-hydroxy-1α-isopropyl-2β-naphthyl)ethyl p-toluenesulphonate and 3,4-dihydro-4-methyl-1-[4-(methylamino)butyl]-2H-1,4-benzodiazepine-2,5-(1H)-dione there is obtained 1-[4-[[2-[[1S,2S]-6-fluoro-1,2,3,4-tetrahydro-2-hydroxy-1-isopropyl-2-naphthyl]ethyl]methylamino]butyl]-3,4-dihydro-4-methyl-2H-1,4-benzodiazepine-2.5-(1H)-dione. MS: M+ 509.

In an analogous manner to that described above, starting from 2-(6-fluoro-1,2,3,4-tetrahydro-2-hydroxy-1α-isopropyl-2β-naphthyl)ethyl p-toluenesulphonate and (S)-6-chloro-1,2,3,11a-tetrahydro-5H-pyrrolo[2,1-c][1,4]benzodiazepine-5.11-(10H)-dione there was prepared (S)-6-chloro-10-[4-[[2-[[1S,2S]-6-fluoro-1,2,3,4-tetrahydro-2-hydroxy-1-isopropyl-2-naphthyl]ethyl]methylamino]butyl]-1,2,3,11a-tetrahydro-5H-pyrrolo[2,1-c][1,4]benzodiazepine-5,11-(10H)-dione, MS: M+ 570.

The 3,4-dihydro-4-methyl-1-[4-(methylamino)butyl]-2H-1,4-benzodiazepine-2,5-(1H)-dione used as the starting material was prepared as follows:

10 g (40 mmol) of 4-[1-(benzyloxy)-N-methylformamido]butyric acid are dissolved in 200 ml of ethanol and treated with 1 ml of concentrated sulphuric acid. Thereafter, the reaction mixture is heated to reflux for 4 hours and the solvent is subsequently evaporated off. The reaction product is then extracted with methylene chloride/saturated sodium bicarbonate solution. After drying and evaporation of the extract there are obtained 9.24 g of a brown oil which is dissolved in 200 ml of tetrahydrofuran, treated with 7.1 ml of 10M boron methylsulphide complex and heated to reflux for 2 hours. Thereafter, the reaction mixture is left to stand at room temperature overnight and then sufficient methanol is slowly added thereto so that gas evolution no longer occurs. In this manner there is obtained a clear solution which is evaporated. The residue obtained (8.09 g) is chromatographed on silica gel with a 1:1 mixture of ethyl acetate and hexane, whereby there are obtained 6.82 g (72%) of benzyl (4-hydroxybutyl)methylcarbamate which is used directly in the next step.

6.75 g (28.4 mmol) of the carbamate obtained above and 10.0 g (52.5 mmol) of p-toluenesulphonyl chloride are dissolved in 25 ml of pyridine at 0°. After standing for 6 hours the mixture is added to ice and extracted with ether. The ether extract is washed with 4N hydrochloric acid, saturated sodium bicarbonate solution and saturated sodium chloride solution, dried and evaporated. In this manner there are obtained 9.38 g (84%) of a yellowish oil of benzyl methyl [4-[(p-toluenesulphonyl)oxy]butyl]-carbamate which is processed directly.

1.9 g (10 mmol) of 4-methyl-3H-1,4-benzodiazepine-2,5-(1H,4H)-dione are dissolved in 20 ml of dimethylformamide and added to a suspension of 430 mg (10 mmol) of 55% sodium hydride in 50 ml of dimethylformamide. 30 minutes after the addition a solution of 3.91 g (10 mmol) of benzyl methyl [4-[(p-toluenesulphonyl)oxy]butyl]carbamate in 20 ml of dimethylformamide is added and the whole reaction mixture is stirred at room temperature for 20 hours. Thereafter, the solvent is evaporated under reduced pressure at 50° and water is subsequently added. After two-fold extraction with methylene chloride the solvent is again evaporated and the residue is chromatographed on silica gel with a 20:1 mixture of methylene chloride and methanol, whereby there are obtained 3.92 g (95.8%) of benzyl methyl [4-(2,3,4,5-tetrahydro-4-methyl-2,5-dioxo-1H-1,4-benzodiazepin-1-yl)butyl]carbamate, MS: M+ 409.

The above carbamate is converted in an analogous manner to that described in Example 7, last paragraph, into the desired 3,4-dihydro-4-methyl-1-[4-(methylamino)butyl]-2H-1,4-benzodiazepine-2,5-(1H)-dione which is used directly in the next step.

In an analogous manner to that described above, starting from benzyl methyl-[4-[(p-toluenesulphonyl)oxy]butyl]carbamate by reaction with the corresponding benzodiazepine there was prepared (S)-6-chloro-1,2,3,11a-tetrahydro-10-[4-(methylamino)butyl]-5H-pyrrolo[2,1-c][1,4]benzodiazepine-5,11-(10H)-dione.

EXAMPLE 41

The following compounds were prepared in an analogous manner to that described in Example 8 by methoxy-acetylating the corresponding hydroxy derivatives:

[1S,2S]-6-fluoro-1,2,3,4-tetrahydro-1-isopropyl-2-[2-[[4-(2,3,4,5-tetrahydro-4-methyl-2,5-dioxo-1H-1,4-benzodiazepin-1-yl)butyl]methylamino]ethyl]-2-naphthyl methoxyacetate hydrochloride, $[\alpha]_{589}^{20} = +28.2°$ (c=0.5%; methanol);

[1S,2S]-2-[2-[[4-[(S)-6-chloro-2,3,11,11a-tetrahydro-5.11-dioxo-1H-pyrrolo[2.1-c][1.4]benzodiazepin-10(5H)-yl]butyl]methylamino]ethyl]-6-fluoro-1,2,3,4-tetrahydro-1-isopropyl-2-naphthyl methoxyacetate hydrochloride, $[\alpha]_{589}^{20} = +215.2°$ (c=0.5%; methanol).

EXAMPLE A

Tablets

| | Composition: | |
|---|---|---|
| (1) | 2-[2-[[3-(2-Benzimidazolyl)propyl]methylamino]ethyl]-6-fluoro-1,2,3,4-tetrahydro-1α-isopropyl-2α-naphthyl methoxyacetate hydrochloride | 75 mg |
| (2) | Lactose powdered | 135 mg |
| (3) | Maize starch white | 55 mg |
| (4) | Povidone K 30 (polyvinylpyrrolidone) | 15 mg |
| (5) | Maize starch white | 15 mg |
| (6) | Talc | 3 mg |
| (7) | Magnesium stearate | 2 mg |
| | Tablet weight | 300 mg |

Manufacturing procedure:

1-3 are mixed intensively. The mixture is thereafter moistened with an aqueous solution of 4 and kneaded, and the resulting mass is granuolated, dried and sieved. The granulate is mixed with 5-7 and pressed to tablets of suitable size.

EXAMPLE B

| Tablets Composition: | | |
|---|---|---|
| (1) 2-[2-[[3-(2-Benzimidazolyl)-propyl]methylamino]ethyl]-6-fluoro-1,2,3,4-tetrahydro-1α-isopropyl-2α-naphthyl methoxyacetate hydrochloride | 75 mg | 60 mg |
| (2) Lactose powdered | 100 mg | 100 mg |
| (3) Maize starch | 60 mg | 60 mg |
| (4) Povidone K 30 (polyvinylpyrrolidone) | 5 mg | 5 mg |
| (5) Maize starch | 15 mg | 15 mg |
| (6) Sodium carboxymethylstarch | 5 mg | 5 mg |
| (7) Talc | 3 mg | 3 mg |
| (8) Magnesium stearate | 2 mg | 2 mg |
| Tablet weight | 265 mg | 250 mg |

Manufacutring procedure:

1-3 mixed intensively. The mixture is thereafter moistened with an aqueous solution of 4 and kneaded, and the resulitng mass is granulated, dried and sieved. The granulate is mixed with 5-8 and pressed to tablets of suitable size.

EXAMPLE C

| Tablets Composition: | | |
|---|---|---|
| (1) 2-[2-[[3-(2-Benzimidazolyl)-propyl]methylamino]ethyl]-6-fluoro-1,2,3,4-tetrahydro-1α-isopropyl-2α-naphthyl methoxyacetate hydrochloride | 75 mg | 90 mg |
| (2) Lactose powdered | 46 mg | 46 mg |
| (3) Cellulose microcrystalline | 60 mg | 60 mg |
| (4) Povidone K 30 (polyvinylpyrrolidone) | 10 mg | 10 mg |
| (5) Sodium carboxymethylstarch | 4 mg | 4 mg |
| (6) Talc | 3 mg | 3 mg |
| (7) Magnesium stearate | 2 mg | 2 mg |
| Tablet weight | 200 mg | 215 mg |

Manufacturing procedure:

1-3 are mixed intensively. The mixture is therafter moistened with an aqueous solution of 4 and kneaded, and the resulting mass is granulated, dried and sieved. The granulate is mixed with 5-7 and pressed to tablets of suitable size.

EXAMPLE D

| Capsules Composition: | |
|---|---|
| (1) 2-[2-[[3-(2-Benzimidazolyl)propyl]methyl-amino]ethyl]-6-fluoro-1,2,3,4-tetrahydro-1α-isopropyl-2α-naphthyl methoxyacetate hydrochloride | 75 mg |
| (2) Lactose crystalline | 100 mg |
| (3) Maize starch white | 20 mg |
| (4) Talc | 9 mg |
| (5) Magnesium stearate | 1 mg |
| Capsule fill weight | 205 mg |

Manufacturing procedure:

The active substance is mixed intensively with the lactose. This mixture is thereafter admixed with the maize starch, the talc and the magnesium stearate, and the mixtture is filled into capsules of suitable size.

EXAMPLE E

| Capsules Composition: | |
|---|---|
| (1) 2-[2-[[3-(2-Benzimidazolyl)propyl]methyl-amino]ethyl]-6-fluoro-1,2,3,4-tetrahydro-1α-isopropyl-2α-naphthyl methoxyacetate hydrochloride | 75 mg |
| (2) Cellulose microcrystalline | 100 mg |
| (3) Sodium carboxymethylstarch | 5 mg |
| (4) Talc | 9 mg |
| (5) Magnesium stearate | 1 mg |
| Capsule fill weight | 190 mg |

Manufacturing procedure:

The active substance is mixed intesnively with the cellulose. This mixture is thereafter admixed with the odium carboxymethylstarch, the talc and the magniesium stearate, and the mixture is filled into capsules of suitable size.

EXAMPLE F

| Injection solution | |
|---|---|
| | 1 ml |
| 2-[2-[[3-(2-Benzimidazolyl)propyl]methyl-amino]ethyl]-6-fluoro-1,2,3,4-tetrahydro-1α-isopropyl-2α-naphthyl methoxyacetate hydrochloride | 8 mg |
| Sodium chloride crystalline pure | 8.5 mg |
| Water for injection ad | 1 ml |

EXAMPLE G

When the procedures described in Examples A-F are followed. tablets, capsules and injection preparations can be manufactured from the following, likewise preferred, compounds and their pharmaceutically usable salts:

[1S,2S]-2-[2-[[3-(2-benzyimidazolyl)propyl]methylamino]ethyl]-6-fluoro-1,2,3,4-tetrahydro-1-isopropyl-2-naphthyl methoxyacetate hydrochloride,

[1S,2S]-2-[2-[[5-(2-benzthiazolyl)pentyl]methylamino]ethyl]-6-fluoro-1,2,3,4-tetrahydro-1-isopropyl-2-naphthyl methoxyacetate hydrochloride.

We claim:

1. A compound of the formula

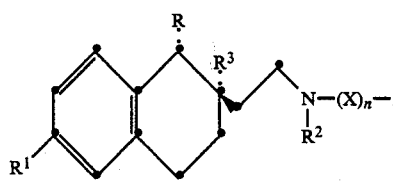

I wherein R is lower-alkyl, $R^1$ is halogen, $R^2$ is $C_1$–$C_{12}$-alkyl, $R^3$ is hydroxy, lower-alkoxy, lower-alkylcarbonyloxy, lower-alkoxy-lower-alkylcarbonyloxy, lower-alkylaminocarbonyloxy; or arylaminocarbonyloxy or aryl-lower-alklaminocarbonyloxy, wherein aryl is phenyl or phenyl mono- or multiplysubstituted by halogen, trifluoromethyl, lower-alkyl, lower-alkoxy, nitro or amino; X is $C_1$–$C_{18}$-alkylene which can be interrupted by 1,4-phenylene or interrupted or lengthened by 1,4-cyclohexylene, A is di- or tri-substituted 2-imidazolyl attached via an ethylene group wherein the substituents are selected from the group consisting of lower alkyl and phenyl; or a substituted or unsubstituted heterocycle selected from the group consisting of benzimidazolyl, benzimidazolonyl, imidazo[4,5-c]pyridinyl, imidazo-[4,5c]pyridinonyl, benzthiazolyl, benzodiazepine-2,5-dion-1-yl and pyrrol[2,1-c][1,4]benzodiazepine-5,11-dion-10-yl wherein the substituents are selected from the group consisting of $C_1$–$C_{12}$-alkyl, phenyllloweralkyl, halo, morpholinoethyl and pyridylmethyl and wherein the last two of said heterocycles may be partially hydrogenated; and n is number 0 or 1, in the form of a racemate or an optical antipode, an N-oxide, or a pharmaceutically usable acid addition salt thereof.

2. A compound in accordance with claim 1, wherein R is isopropyl.

3. A compound in accordance with claim 2, wherein $R^3$ is hydroxy, lower-alkylcarbonyloxy, lower-alkoxy-lower-alkylcarbonyloxy or lower-alkylaminocarbonyloxy.

4. A compound in accordance with claim 3, wherein $R^3$ is isobutyryloxy, methoxyacetyloxy or butylaminocarbonyloxy.

5. A compound in accordance with claim 1, wherein n is the number 1.

6. A compound in accordance with claim 1, wherein $R^1$ is fluorine.

7. A compound in accordance with claim 1, wherein $R^2$ is methyl.

8. A compound in accordance with claim 1, wherein X is $C_3$–$C_7$-alkylene.

9. A compound in accordance with claim 8, wherein X is propylene, butylene, pentamethylene or hexamethylene.

10. A compound in accordance with claim 1, wherein A is 2-benzimidazolyl, 2-benzthiazolyl, 1-methyl-2-benzimidazolyl, 1-dodecyl-2-benzimidazolyl, benzimidazolonyl, 2,3,4,5-tetrahydro-4-methylbenzodiazepine-2,5-dion-1-yl, 6-chloro-2,3,11,11a-tetrahydro-pyrrolo[2,1-c][1,4]benzodiazepine-5,11-dion-10-yl or 1-methyl-4,5-diphenyl-2-imidazolyl.

11. A compound in accordance with claim 10, wherein A is 2-benzimidazolyl or 2-benzthiazolyl.

12. A compound in accordance with claim 1, wherein R is isopropyl, $R^3$ is hydroxy, isobutyryloxy, methoxyacetyloxy or butylaminocarbonyloxy, $R^1$ is fluorine, $R^2$ is methyl, X is propylene, butylene, pentamethylene or hexamethylene, A is 2-benzimidazolyl or 2-benzthiazolyl and n is the number 1.

13. A compound in accordance with claim 1, 2-[2-[[3-(2-benzimidaolyl)propyl]methylamino]ethyl]-6-fluoro-1,2,3,4-tetrahydro-1α-isopropyl-2α-naphthyl methoxyacetate.

14. A compound in accordance with claim 1, [1S,2S]-2-[2-[[5-(2-benzthiazolyl)pentyl]methylamino]ethyl]-6-fluoro-1,2,3,4-tetrahydro-1-isopropyl-2naphthyl methoxyacetate.

15. A compound in accordance with claim 1, [1S,2S]-2-[2-[[3-(2-benzimidazolyl)propyl]methylamino]ethyl]-6-fluoro-1,2,3,4-tetrahydro-1-isopropyl-2-naphthyl methoxyacetate.

16. A composition with calcium antagonistic activity comprising a calcium antagonistically effective amount of a compound of the formula

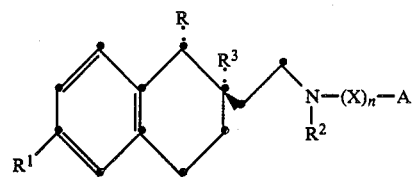

wherein R is lower-alkyl, $R^1$ is halogen, $R^2$ is $C_1$–$C_{12}$-alkyl, $R^3$ is hydroxy, lower-alkoxy, lower-alklcarbonyloxy, lower-alkoxy-lower-alkylcarbonyloxy, lower-alkylaminocarbonyloxy; or arylamiocarbonyloxy or aryl-lower-alkylaminocarbonyloxy, wherein aryl is phenyl or phenyl mono- or multiply-substituted by halogen, trifluoromethyl, lower-alkyl, lower-alkoxy, niro or amino; X is $C_1$–$C_{18}$-alkylene which can be intrrupted by 1,4-phenylene or interrupted or lengthened by 1,4-cyclohexylene, A is di- or tri-substituted 2-imidazolyl attached via an ethylene group wherein the substituents are selected from the group consisting of lower alkyl and phenyl; or a substituted or unsubstituted heterocycle selected from the group consisting of benzimidazolyl, benzimidazolonyl, imidazol[4,5-c]pyridinyl, imidazo-[4,5-c]pyridinyl, benzthiazolyl, benzodiazepine-2,5-dion-1-yl and pyrrol[2,1-c][1,4benzodiazepine-5,11-dion-10-yl wherein the substituents are selected from the group consisting of $C_1$–$C_{12}$-alkyl phenylloweralkyl, halo, morpholinoethyl and pyridylmethyl and wherein the last two of said heterocycles may be partially hydrogenated; and n is the number 0 or 1, in the form of a racemate or an optical antipode, an N-oxide, or a pharmaceutically usable acid addition salt thereof, and a pharmaceutically inert excipient.

17. A composition in accordance with claim 16, wherein R is isopropyl, $R^3$ is hydroxy, isobutyryloxy, methoxyacetyloxy or butylaminocarbonyloxy, $R^1$ is fluorine, $R^2$ is methyl, X is propylene, butylene, pentamethylene or hexamethylene, A is 2-benzimidazolyl or 2-benzthiazolyl and n is the number 1.

18. A composition in accordance with claim 17, wherein the compound of formula I is [1S,2S]-2-[2-[[3-(2-benzimidazolyl)propyl]methylamio]ethyl]-6-fluoro-1,2,3,4-tetrahydro-1-isopropyl-2-naphthyl methoxyacetate or its racemate.

19. A method of treating or preventing angina petcoris, ischaemia, arrhydthmias, high blood pressure and cardiac insufficiency which comprises administering to a warm-blooded animal in need of such treatment, a calcuim antagonistically effective amount of a compound of the formula

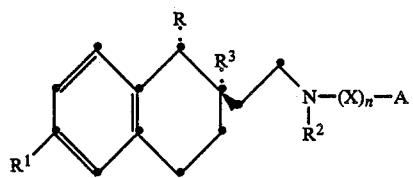

wherein R is lower-alkyl, $R^1$ is halogen, $R^2$ is $C_1$–$C_{12}$-alkyl, $R^3$ is hydroxy, lower-alkoxy, lower-alkylcarbonyloxy, lower-alkoxy-lower alkylcarbonyloxy, lower-alkylaminocarbonyloxy; or, arylaminocarbonyloxy or aryl-lower-alkylamiocarbonyloxy wherein aryl is phenyl or phenyl mono- or multiplysubstituted by halogen, trifluoromethyl, lower-alkyl, lower-alkoxy, nitro or amino; X is $C_1$–$C_{18}$-alkylene which can be interrupted by 1,4-phenylene or interrupted or lengthened by 1,4-cyclohexylene, A is di- or tri-substituted 2-imidazolyl attached via an ethylene group wherein the substituents are selected from the group consisting of lower alkyl and phenyl; or a substituted or unsubstituted heterocycle selected from the group consisting of benzimidazolyl, benzimidazolonyl, imidazo[4,5-c]pyridinyl, imidazo[4,5-c]pyridinonyl, bezthiazoyl, benzodiazepine-2,5-dion-1-yl and pyrrolo[2,1-c][1,4]benzodiazepine-5,11-dion-10-yl wherein the substitutents are selected from the group consisting of $C_1$–$C_{12}$-alkyl, phenylloweralkyl, halo, morpholinoethyl and pyridylmethyl and wherein the last two of said heterocycles may be partially hydrogenated; and n is the number 0 or 1, in the form of a racemate or an optical antipode, an N-oxide, or a phamraceutically usable acid addition salt thereof.

20. A method in accordance with claim 19 wherein R is isopropyl, $R^3$ is hydroxy, isobutyryloxy, methoxyacetyloxy or butylaminocarbonyloxy, $R^1$ is fluorine, $R^2$ is methyl, X is propylene, butylene, pentamethylene or hexameethylene, A is 2-benzimidazolyl or 2-benzthiazolyl and n is the number 1.

21. A method in accordance with claim 20, wherein the compound of formula I is [1S,2S]-2-[2-[[3-(2-benzimidazolyl)propyl]methylamino]ethyl]-6-fluoro-1,2,3,4-tetrahydro-1-isopropyl-2-naphthyl methoxyacetate or its racemate.

* * * * *

UNITED STATES PATENT AND TRADEMARK OFFICE
CERTIFICATE OF CORRECTION

PATENT NO. : 4,808,605
DATED : February 28, 1989
INVENTOR(S) : Quirico Branca, Roland Juanin, Hans Peter Märki, Fränz Marti, Henri Ramuz Page 1 of 9

It is certified that error appears in the above-identified patent and that said Letters Patent is hereby corrected as shown below:

Column 2, line 11, "and the 106 like" should read
--- and the like --- .

Column 8, line 42, "acidiin" should read
--- acid in --- .

Column 14, line 63, in the Table, letter G "[1S,2S]-2,6-Fluoro" should read --- [1S,2S]-6-Fluoro --- .

Columns 17-18, line 40, "heated to 0°" should read
--- heated to 70° --- .

Column 18, line 52, "[1S,2S]-2-[2755- " should read
--- [1S,2S]-2-[2-   --- .

Column 19, lines 12-13, "-isopropyl-2β-naphthalenol" should read   --- -isopropyl-2-naphthalenol   --- .

Column 19, line 15, "1α-isopropyl-2β-naphthyl" should read   --- 1α-isopropyl-2β-naphthyl --- .

Column 20, line 38, "Thereafter." should read
--- Thereafter, --- .

Column 21, line 65, "(37.2% of" should read
--- (37.2%) of   --- .

Column 22, line 4, "of 6997-fluoro" should read
--- of 6-fluoro --- .

UNITED STATES PATENT AND TRADEMARK OFFICE
CERTIFICATE OF CORRECTION

PATENT NO. : 4,808,605
DATED : February 28, 1989
INVENTOR(S) : Quirico Branca, Roland Juanin, Hans Peter Märki, Fränz Marti, Henri Ramuz It is certified that error appears in the above-identified patent and that said Letters Patent is hereby corrected as shown below:

Column 22, line 5, "tetrahydro-2-isopropyl-2-hydroxy" should read --- tetrahydro-2-hydroxy --- .

Column 23, line 34, "an anaoogous manner" should read --- an analogous manner --- .

Column 25, line 22, "water.dried over" should read --- water, dried over --- .

Column 26, line 6, "Thereafter." should read --- Thereafter, --- .

Column 26, line 21, "benzimiaazolinyl]" should read --- benzimidazolinyl- --- .

Column 26, line 58, "1-[6-[[2-[[7S,2S]- " should read --- 1-[6-[[2-[[1S,2S]- --- .

Column 27, line 37, "analoqous" should read --- analogous --- .

Column 28, line 53, "2hydroxy-" should read --- 2-hydroxy- --- .

Column 29, line 47, "anaIogous" should read --- analogous --- .

UNITED STATES PATENT AND TRADEMARK OFFICE
CERTIFICATE OF CORRECTION

PATENT NO. : 4,808,605
DATED : February 28, 1989
INVENTOR(S) : Quirico Branca, Roland Juanin, Hans Peter Märki, Fränz Marti, Henri Ramuz It is certified that error appears in the above-identified patent and that said Letters Patent is hereby corrected as shown below:

Column 29, line 47, "lhat" should read --- that --- .

Column 30, line 4, "With" should read --- with --- .

Column 30, line 22, "1.2,3,4-tetrahydro" should read --- 1,2,3,4-tetrahydro --- .

Column 30, line 53, "[4.5-c]" should read --- [4,5-c] --- .

Column 30, line 55, "[4.5-c]" should read --- [4,5-c] --- .

Column 32, line 24, "water." should read --- water, --- .

Column 32, line 44, " (0 005 mol)" should read --- (0.005 mol) --- .

Column 33, line 10, " -4.5-" should read --- -4,5- --- .

Column 33, line 15, "sodium chloride.dried" should read --- sodium chloride, dried --- .

UNITED STATES PATENT AND TRADEMARK OFFICE
CERTIFICATE OF CORRECTION

PATENT NO. : 4,808,605  
DATED : February 28, 1989  
INVENTOR(S) : Quirico Branca, Roland Juanin, Hans Peter Märki, Fränz Marti, Henri Ramuz Page 4 of 9

It is certified that error appears in the above-indentified patent and that said Letters Patent is hereby corrected as shown below:

Column 33, line 57, " N-methyl-4.5- " should read --- -N-methyl-4,5- --- .

Column 34, line 55, " -4.5- " should read --- -4,5- --- .

Column 34, line 59, "analoqous" should read --- analogous --- .

Column 35, line 17, " (ppE)" should read --- (PPE) --- .

Column 35, line 21, "minuIes" should read --- minutes --- .

Column 35, lines 46-47, " [5.4,0] " should read --- [5.4.0] --- .

Column 35, lines 65-66, "0 12mol)" should read --- (0.12) --- .

Column 36, line 3, "The organic phase." should read --- The organic phase, --- .

Column 36, line 19, "The product.isolated" should read --- The product, isolated --- .

UNITED STATES PATENT AND TRADEMARK OFFICE
CERTIFICATE OF CORRECTION

PATENT NO. : 4,808,605

DATED : February 28, 1989

INVENTOR(S) : Quirico Branca, Roland Juanin, Hans Peter Märki, Fränz Marti, Henri Ramuz It is certified that error appears in the above-identified patent and that said Letters Patent is hereby corrected as shown below:

Column 37, line 36, "analoqous" should read --- analogous --- .

Column 37, line 49, "A solutionof" should read --- A solution of --- .

Column 37, line 64, "ice-water The" should read --- ice-water. The --- .

Column 39, line 15, "The product.isolated in" should read --- The product, isolated in --- .

Column 39, line 31, " -1,4-benzodiazepine-2.5-(1H)- " should read --- -1,4-benzodiazepine-2,5-(1H)- --- .

Column 39, line 37, " [1,4]benzodiazepine-5.11-(10H) " should read --- [1,4]benzodiazepine-5,11-(10H) --- .

Column 40, lines 47-48, " -5.11- " should read --- -5,11- --- .

UNITED STATES PATENT AND TRADEMARK OFFICE
CERTIFICATE OF CORRECTION

PATENT NO. : 4,808,605
DATED : February 28, 1989
INVENTOR(S) : Quirico Branca, Roland Juanin, Hans Peter Märki, Fränz Marti, Henri Ramuz It is certified that error appears in the above-indentified patent and that said Letters Patent is hereby corrected as shown below:

Column 40, line 48, " [2.1-c][1.4] " should read --- [2,1-c][1,4] --- .

Column 41, line 3, " granuolated " should read --- granulated --- .

Column 41, line 25, "Manufacutring" should read --- Manufacturing --- .

Column 41, line 28, "resulitng" should read --- resulting --- .

Column 41, line 49, "therafter" should read --- thereafter --- .

Column 42, line 5, "mixtture" should read --- mixture --- .

Column 42, line 22, "intesnively" should read --- intensively --- .

Column 42, line 24, "odium" should read --- sodium --- .

Column 42, lines 24-25, "magniesium" should read --- magnesium --- .

Column 42, line 41, "followed.tablets" should read --- followed, tablets --- .

UNITED STATES PATENT AND TRADEMARK OFFICE
CERTIFICATE OF CORRECTION

PATENT NO. : 4,808,605
DATED : February 28, 1989
INVENTOR(S) : Quirico Branca, Roland Juanin, Hans Peter Märki, Fränz Marti, Henri Ramuz It is certified that error appears in the above-indentified patent and that said Letters Patent is hereby corrected as shown below:

Column 42, line 67, "alklaminocarbonyloxy" should read --- alkylamino-carbonyloxy --- .

Column 42, line 68, "multiplysubstituted" should read --- multiply-substituted --- .

Column 43, line 10, "[4,5c]" should read --- [4,5-c] --- .

Column 43, line 55, " (2-benzimidaolyl)" should read ---  -(2-benzimidazolyl) --- .

Column 44, lines 11-12, "lower-alklcarbonyloxy" should read ---  -lower-alkyl-carbonyloxy  --- .

Column 44, line 13, "arylamio-carbonyloxy" should read --- arylaminocarbonyloxy --- .

Column 44, line 17, "niro" should read --- nitro --- .

Column 44, lines 18-19, "intrrupted" should read --- interrupted --- .

Column 44, line 25, "pyridinyl" should read --- pyridinonyl --- .

UNITED STATES PATENT AND TRADEMARK OFFICE
CERTIFICATE OF CORRECTION

PATENT NO. : 4,808,605
DATED : February 28, 1989
INVENTOR(S) : Quirico Branca, Roland Juanin, Hans Peter Märki, Fränz Marti, Henri Ramuz It is certified that error appears in the above-indentified patent and that said Letters Patent is hereby corrected as shown below:

Column 44, lines 27-28, "[1,4benzodiazepine-" should read ---[1,4]benzodiazepine---.

Column 44, line 44, "(2-benzimidazolyl)propyl]methyl-amio]ethyl " should read ---(2-benzimidazolyl)propyl]methyl- amino]ethyl --- .

Column 44, lines 47-48, "petcoris" should read --- pectoris --- .

Column 44, line 48, "arrhydthmias" should read --- arrhythmias --- .

Column 44, line 51, "calcuim" should read --- calcium --- .

Column 44, line 66, "aryl-lower-alkylamio-carbonyloxy" should read ---aryl-lower-alkyl-aminocarbonyloxy--- .

Column 44, line 67, "multiplysubstituted" should read --- multiply-substituted --- .

Column 45, line 9, "bezthiazoyl" should read --- benzthiazolyl --- .

UNITED STATES PATENT AND TRADEMARK OFFICE
CERTIFICATE OF CORRECTION

PATENT NO. : 4,808,605
DATED : February 28, 1989
INVENTOR(S) : Quirico Branca, Roland Juanin, Hans Peter Märki, Fränz Marti, Henri Ramuz It is certified that error appears in the above-indentified patent and that said Letters Patent is hereby corrected as shown below:

```
Column 46, line 2, "phamraceutically" should read
--- pharmaceutically --- .

Column 46, line 4, "Claim 19 wherein" should read
--- Claim 19, wherein --- .

Column 46, line 8, "hexameethylene" should read
--- hexamethylene --- .
```

Signed and Sealed this

Seventeenth Day of October, 1995

Attest:

BRUCE LEHMAN

Attesting Officer

Commissioner of Patents and Trademarks